(12) United States Patent
Bollen et al.

(10) Patent No.: US 10,441,784 B2
(45) Date of Patent: Oct. 15, 2019

(54) METHOD AND ASSEMBLY FOR THE GENERATION OF SIGNAL SHAPES FOR HEALING WOUNDS BY ELECTRO-STIMULATION

(71) Applicant: Q CARE MEDICAL SERVICES, Diepenbeek (BE)

(72) Inventors: Marc Bollen, Oreye (BE); Filip Ponsaerts, Zoutleeuw (BE)

(73) Assignee: Q Care Medical Services, Diepenbeek (BE)

( * ) Notice: Subject to any disclaimer, the term of this patent is extended or adjusted under 35 U.S.C. 154(b) by 8 days.

(21) Appl. No.: 15/378,643

(22) Filed: Dec. 14, 2016

(65) Prior Publication Data

US 2017/0151431 A1 Jun. 1, 2017

Related U.S. Application Data

(62) Division of application No. 14/232,998, filed as application No. PCT/IB2012/053636 on Jul. 16, 2012, now abandoned.

(30) Foreign Application Priority Data

Jul. 15, 2011 (BE) .................................. 2011/0457

(51) Int. Cl.
*A61N 1/20* (2006.01)
*A61N 1/04* (2006.01)
(Continued)

(52) U.S. Cl.
CPC ........... *A61N 1/205* (2013.01); *A61N 1/0468* (2013.01); *A61N 1/0492* (2013.01); *A61N 1/326* (2013.01);
(Continued)

(58) Field of Classification Search
None
See application file for complete search history.

(56) References Cited

U.S. PATENT DOCUMENTS 4,690,145 A * 9/1987 King-Smith ....... A61N 1/36021
607/63
5,269,304 A * 12/1993 Matthews ................ A61N 1/40
607/148
(Continued)

FOREIGN PATENT DOCUMENTS

WO 02/41942 5/2002
WO 2006/102420 9/2006
WO 2010/132923 11/2010

*Primary Examiner* — Erica S Lee
(74) *Attorney, Agent, or Firm* — Jacobson Holman PLLC

(57) ABSTRACT

A method for generating a signal shape (w1) for an electro-stimulation signal (w1) for healing wounds by electro-stimulation by way of an electrode (E1) which has an encoding member (6) with a code word (cw) which identifies therapeutic treatments, and is coupled to indicators (i1, i2) which indicate which treatments have to be activated. The signal shape (w1) is formed systematically from base signals capable of being parameterized such as a DC signal and two pulse trains, the parameters and the timing of which are formed systematically and applied where necessary, in accordance with the combined therapies. The generation of signal shapes for a plurality of electrodes is also disclosed.

18 Claims, 19 Drawing Sheets

(51) Int. Cl.
    *A61N 1/32*         (2006.01)
    *A61N 1/36*         (2006.01)
    *A61N 1/375*       (2006.01)

(52) U.S. Cl.
    CPC ..... *A61N 1/36014* (2013.01); *A61N 1/36021* (2013.01); *A61N 1/3752* (2013.01)

(56) References Cited

U.S. PATENT DOCUMENTS

| | | | |
|---|---|---|---|
| 6,584,358 B2* | 6/2003 | Carter | A61N 1/36021 607/46 |
| 2003/0074025 A1 | 4/2003 | Wuthrich | |
| 2009/0209958 A1 | 8/2009 | Davison | |
| 2010/0125312 A1* | 5/2010 | Stevenson | A61N 1/37288 607/45 |
| 2012/0016446 A1* | 1/2012 | Panting | A61N 1/0484 607/62 |

\* cited by examiner

Fig 11A Fig 11B Fig 11C Fig 11D

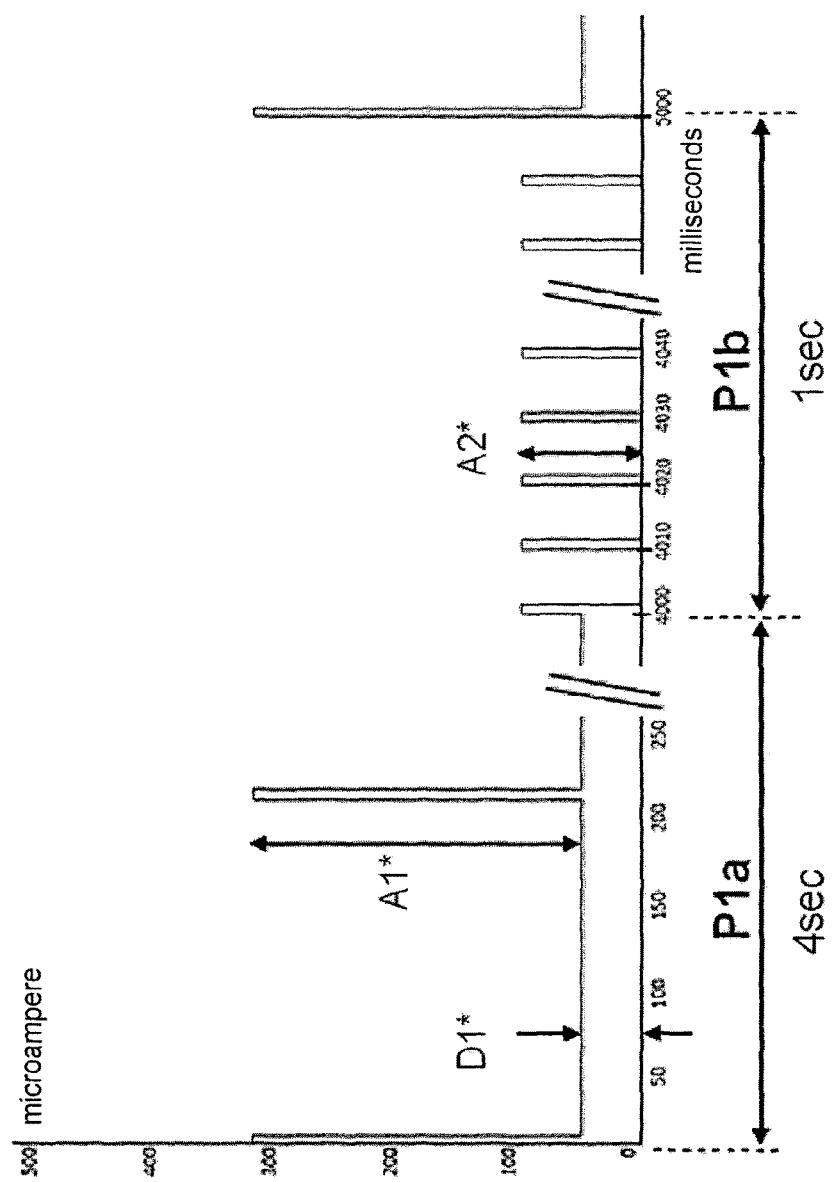

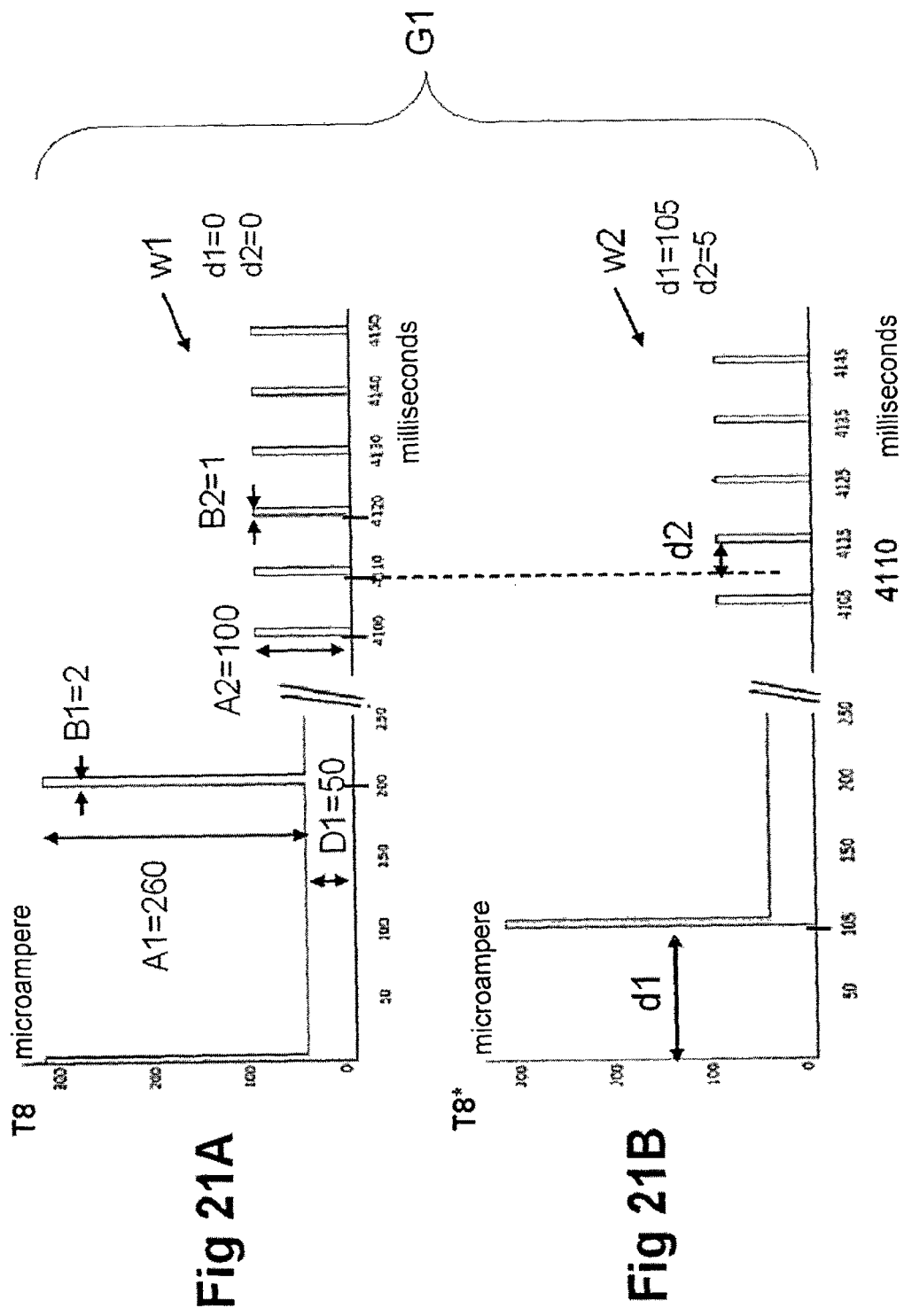

METHOD AND ASSEMBLY FOR THE GENERATION OF SIGNAL SHAPES FOR HEALING WOUNDS BY ELECTRO-STIMULATION

FIELD OF THE INVENTION

The invention relates to a method of generating a signal shape from an electro-stimulation signal to be supplied to an electrode for healing wounds by electro-stimulation, as well as an assembly for performing this method.

PRIOR ART

Human and animal tissue can be damaged in different ways, and this can result inter alia in acute and chronic wounds, trauma and infected or necrotic tissue. In human and animal tissue a healing process will normally start in order to repair the damage. In the case of permanent damage, a chronic state or infection, these mechanisms will take place slowly or even cease, with the possible consequence of long-lasting infection, pain, immobility and scar formation. Micro-current therapy for the care of wounds has been investigated for decades and a large number of in vitro, in vivo and clinical studies are available in which the therapeutic effect has been demonstrated. Present-day applications of electrotherapy focus primarily on the management and control of pain, whereas it should also be possible for electrotherapy to be used for other purposes.

Various apparatus for the care of wounds are commercially available. As a rule, these are apparatus which are linked to one or more sets of two electrodes and which are then positioned in the vicinity of the wound. Not all these apparatus, however, use micro current ("micro current electrotherapy", abbreviated to MET), but some are TENS ("transcutaneous electrical nerve stimulation") apparatus. The difference lies in the generated wave shape in which a key criterion for distinguishing between micro current and TENS is the maximum intensity of the electrical signal intended for therapy. In the case of micro current, signals with an intensity lower than 1 mA (milliamp) are generated, whereas in the case of TENS this is typically a few mA to tens of mA. Micro-current therapy is intended to work at the cell level, not on muscles or nerves. TENS will directly stimulate nerves, and it is more suitable as a therapy for pain control.

Although some electro-stimulation apparatus are able to generate a complex wave shape for the treatment of various syndromes, which wave shape can be provided for treatment by way of electrodes positioned inside or outside the wound, it is frequently not easy for the nursing staff to set it. In this case it is even possible for mistakes to be made in the setting, as a result of which the therapeutic effect may be lost or may even cause an opposite effect.

WO 02/41942 discloses an electro-acupuncture device with stimulation electrode assembly. The latter device provides pulsed stimulation output of varying power depending on the particular electrode assembly used. The device enables to detect the presence of the electrode and to set operation performance in function of the detected electrode thereby reducing the probability that errors are made in using inappropriate electrodes.

A drawback of the device disclosed in WO 02/41942 is that in case of more than one treatment to be applied the stimulation signals are merely combined, which could cause the application of a combined signal which could harm the patient.

DISCLOSURE OF THE INVENTION

The object of the present invention is to provide a method for the generation of a signal shape from an electro-stimulation signal to be supplied to an electrode for healing wounds by electro-stimulation, in such a way as to minimize the probability that in case of combined signals an incorrect stimulation signal is applied which could lead to an incorrect therapeutic treatment.

This object is attained by a method which is characterized in that before said signal shape is generated the temporary signal shape is checked in order to establish whether or not the temporary signal shape falls within therapeutic limits of the therapeutic treatments identified by each of the signals on which the temporary signal shape was formed, said temporary signal shape being adjusted so as to fall within said therapeutic limits if it has been established that it did not fall within said therapeutic limits In this patent publication the expressions "the indicator indicates activation" and "the indicator is active" are used synonymously.

With therapeutic limits the intention is that the micro current should be high enough to achieve the desired effect, but low enough not to achieve a negative effect. In the case of direct current this means for example that the DC value has to be within certain limits. In the case of a pulse train this means for example that the pulse amplitude, the pulse width and the pulse frequency have to be within certain limits.

Since the electrode comprises an encoding member which comprises a code word which indicates which therapeutic treatment or treatments should be carried out by the electrode in question, the nursing staff need merely select the electrode with the correct encoding member and connect it, instead of having to enter a series of parameters (such as for example frequencies, delays, amplitudes, DC levels, pulse widths etc.) into the apparatus manually. As a result, the possibility of incorrect settings is significantly reduced.

Since no further settings have to be made (such as the turning of knobs and/or the pressing of switches and/or the entering of numbers by way of a numerical keypad), virtually no time is lost for the activation of the apparatus, even for a complex (combined) therapeutic treatment. This reduces costs for the carers, and is pleasant for the patient, particularly when painful wounds are involved.

Since the code word comprises at least two code word portions, it is possible for a complex signal shape to be provided which is suitable for two different therapies on the same wound. This saves the nursing staff from having to change the settings regularly (for each therapy individually), so that the possibility of errors is further reduced, and the efficiency of the staff is further increased.

On account of generating the signal shape on the basis of the indicators which indicate which therapeutic treatment or treatments should be activated, it is possible for the signal shapes to be formed in a systematic manner, in such a way that the final signal shapes do not adversely affect the therapies selected.

On account of forming the signal shape step by step and by producing the temporary signal shape from the already formed signal shape and the further signal, the maximum account can be taken of the temporary signal shape already formed, and in the same way also the history of the code words, indicators and therapies already treated, in such a way that they do not influence one another or influence one another to only a minimal degree.

In order to form the signal shape, first of all the first code word portion is looked at, and if it is active, a first signal is accordingly retrieved and is assigned for example to the temporary signal shape. After that, the second code word portion is looked at, and if the second indicator is also active, a second signal is retrieved, but instead of that usually to alternate in time (time multiplexing) with the first signal, a check is made as to whether adjustments are necessary to one or to both signals, in such a way that the combined signal falls within the therapeutic limits of the combined therapy, and, if necessary, adjustments are carried out. In this way, a signal shape can be generated which always falls within the therapeutic limits of the activated therapies and which is adapted in an optimum manner to the chosen combination of the various therapies as defined by the code word portions and the indicators thereof.

In a first embodiment of the method according to the invention the first signal is a first DC signal with a first DC value and the second signal is a second DC signal with a second DC value:

and the temporary signal shape is formed by taking the first signal over a first period if the first indicator indicates activation, and by taking the second signal over the first period if the first indicator does not indicate activation and the second indicator does indicate activation;

and the further forming of the temporary signal shape on the basis of the first DC signal and the second DC signal comprises changing the first DC value to a DC value lying in a range with the first DC value and the second DC value as the limit values.

In this way, a signal shape can be generated by a combination of two therapies to which a DC signal corresponds each time. In this way, a DC signal is still used, although with a different DC value.

In this case it is preferable for the smallest DC value to be chosen from the first and the second DC values.

It has been found that the smallest DC value usually gives a better result for the joint therapeutic treatment than the larger DC value in order that the therapeutic curves (see for example FIG. 7 and FIG. 8) generally finish more quickly above their optimum value than under their optimum value.

In a second embodiment of the method according to the invention the first signal is a first DC signal with a first DC value and the second signal is a first pulse train with a first frequency lower than a previously defined frequency and with a first pulse amplitude and with a first pulse width;

and the temporary signal shape is formed by taking the first signal over a first period if the first indicator indicates activation, and by taking the second signal over the first period if the first indicator does not indicate activation and the second indicator does indicate activation;

and the further forming of the temporary signal shape on the basis of the first DC signal and the first pulse train comprises splitting the first period into at least one first and at least one second period portion, the first DC value being maintained during the at least one first period portion, and the first DC value being reduced to a reduced DC value during the at least one second period portion, and the first pulse amplitude is reduced to a reduced first pulse amplitude, and the first pulse train with the reduced first pulse amplitude is superimposed upon the first DC signal with the reduced DC value.

It is preferable for the previously defined frequency to be a frequency in the range of from 20 to 50 Hz, preferably virtually equal to 30 Hz. The previously defined frequency is used to make a distinction between a pulse train with a "low" frequency (i.e, lower than 20 Hz) and a pulse train with a "high" frequency (i.e, higher than 50 Hz), since in accordance with the method according to the invention these pulse trains are produced with the temporary signal shape in a different manner.

In the second embodiment a DC signal can be combined with a first pulse train with a "low" frequency (for example 5 Hz). As a result of reducing the DC value and/or the pulse amplitude, one signal shape can be generated for the treatment by the two therapies, without the other therapy being adversely affected. As a result of superimposing the pulse train on the reduced DC signal in the second period portion, the influence of the DC signal is also achieved during the second period portion, in other words the two therapeutic effects are achieved at the same time (during the second period portion).

In a third embodiment of the method according to the invention the first signal is a first DC signal with a first DC value and the second signal is a second pulse train with a second frequency higher than the previously defined frequency and with a second pulse amplitude and with a second pulse width;

and the temporary signal shape is formed by taking the first signal over a first period if the first indicator indicates activation, and by taking the second signal over the first period if the first indicator does not indicate activation and the second indicator does indicate activation;

and the further forming of the temporary signal shape on the basis of the first DC signal and the second pulse train comprises splitting the first period into a plurality of period portions, and the fractioning of each period portion into a first and a second period fraction, the DC signal with the first DC value being maintained during the first period fraction, and the second pulse amplitude being reduced to a reduced second pulse amplitude during the second period fraction, and the DC signal is replaced by the second pulse train with the reduced second pulse amplitude.

In this embodiment a DC signal can be combined with a second pulse train with a "high" frequency (for example 100 Hz).

Comparison of the second and the third embodiments shows that in the case of a pulse train with a "high" frequency the period is fractioned and the signal shape in the second period fraction is substituted. If the pulse train has a "low" frequency, then splitting and superimposition take place in the second period portion. It has been found from tests that a signal shape of this type gives the best therapeutic results.

In a fourth embodiment of the method according to the invention the first signal is a first pulse train with a first frequency lower than the previously defined frequency and with a first pulse amplitude and with a first pulse width, and the second signal is a second pulse train with a second frequency higher than the previously defined frequency and with a second pulse amplitude and with a second pulse width:

and the temporary signal shape is formed by taking the first signal over a first period if the first indicator indicates activation, and by taking the second signal over the first period if the first indicator does not indicate activation and the second indicator does indicate activation;

and the further forming of the temporary signal shape on the basis of the first pulse train and the second pulse train comprises splitting the first period into a plurality of period portions, and the fractioning of each period portion into a plurality of first period fractions and a second period fraction, the first pulse train with the first pulse amplitude being maintained during the first period fraction, and the first pulse train being replaced by the second pulse train during the second period fraction.

In this way, two pulse trains, one with a low frequency and one with a high frequency, can be combined. It should be noted that in this case the amplitude of the two pulse trains need not be reduced, since there is no DC signal.

For the four embodiments described above it is the case that the combined signal shape can be formed on the basis of single simple and basic signals capable of being parameterized such as a DC signal or a pulse train, as a result of which the implementation of the method (for example in hardware or software) can be greatly simplified, and the signal shape for each electrode can be generated on the basis of a small number of parameters. This last likewise allows the adaptation of the signal shapes in the case of combined therapies in a relatively simple manner by way of one electrode, and even the adaptation of a plurality of signal shapes for a plurality of electrodes, as will be explained later. In addition, signals of this type can be generated very simply by digital electronics, in particular by a programmable microprocessor, on account of which the design is highly flexible, and the product is very cheap and highly reliable. Furthermore, it is known that a direct current and a pulse train are well suited for certain therapeutic treatments, provided that their parameters meet certain conditions. It is not known, however, how signals of this type can be combined to form the complex signal which is formed by the method according to the present invention by which various therapies can be combined for the same wound.

An advantage of the way in which a DC signal and a pulse train are combined (for example superimposition in the second embodiment, time multiplexing in the third embodiment, in contrast to analogue modulation techniques for example) is that the therapeutic effects of combined signal shapes of this type can be connected in a comprehensible manner to the respective signal portions, and that the parameters of the signal portions can be optimized in a simple manner during the design and/or evaluation stage, and that there is a negligible impact upon other therapies (for example on account of unknown effects).

In a fifth embodiment of the method according to the invention the code word comprises at least three code word portions, the third code word portion identifying a third therapeutic treatment, and the third code word portion having coupled to it a third indicator which indicates whether the third therapeutic treatment should be activated or not;

and the first signal is a first DC signal with a first DC value, and the second signal is a first pulse train with a first frequency lower than the previously defined frequency and with a first pulse amplitude and with a first pulse width, and the third signal is a second pulse train with a second frequency higher than the previously defined frequency and with a second pulse amplitude and with a second pulse width;

and the temporary signal shape is formed by taking the first signal over a first period if the first indicator indicates activation, and by taking the second signal over the first period if the first indicator does not indicate activation and the second indicator does indicate activation, and by taking the third signal over the first period if both the first and the second indicators do not indicate activation and the third indicator does indicate activation;

and the further forming of the temporary signal shape on the basis of the first DC signal and the first pulse train comprises splitting the first period into at least one first and at least one second period portions; the first DC value being maintained during the at least one first period portion, and the first DC value being reduced to a reduced DC value during the at least one second period portion, and the first pulse amplitude being reduced to a reduced first pulse amplitude, and the first pulse train with the reduced first pulse amplitude is superimposed upon the first DC signal with the reduced DC value;

and the further forming of the temporary signal shape on the basis of the first DC signal and the second pulse train comprises splitting the first period into a plurality of period portions, and the fractioning of each period portion into a first and a second period fraction, the first DC value being maintained during the first period fraction, and the second pulse amplitude being reduced to a reduced second pulse amplitude during the second period fraction, and the DC signal is replaced by the second pulse train with the reduced second pulse amplitude;

and the further forming of the temporary signal shape on the basis of the first pulse train and the second pulse train comprises splitting the first period into a plurality of period portions, and the fractioning of each period portion into a first and a second period fraction, the first pulse train being maintained during the first period fraction, and the first pulse train is replaced by the second pulse train during the second period fraction;

and the further forming of the temporary signal shape on the basis of the first DC signal and the first pulse train and the second pulse train comprises in a first step splitting the first period into a first and a second period portion, the first DC value being maintained during the first period portion, and the first DC value being reduced to a reduced DC value during the second period portion, and the first pulse amplitude is reduced to a reduced first pulse amplitude, and the first pulse train with the reduced first pulse amplitude is superimposed upon the first DC signal with the reduced DC value, and in a second step the fractioning of the first period portion into a plurality of first and second period fractions, the DC signal with the first DC value being maintained during each first period fraction, and the second pulse amplitude is reduced to a reduced second pulse amplitude during each second period fraction, and the DC signal is replaced by the second pulse train with the reduced second pulse amplitude, and the splitting of the second period portion into a plurality of third and fourth period fractions, the DC signal with the reduced DC value with the first pulse train with the reduced first pulse amplitude superimposed upon it being maintained during each third period fraction, and the second pulse amplitude is reduced to a reduced second pulse amplitude during each fourth period fraction, and the DC signal with the reduced DC value with the first pulse train with the reduced first pulse amplitude superimposed upon it is replaced by the second pulse train with the reduced second pulse amplitude.

In this fifth embodiment of the method according to the invention three different signals for three different therapies can be combined into one signal shape in a manner as indicated above. It should be noted that the most complex manner of further formation is the one in which both a DC signal and a first pulse train with a low frequency as well as a second pulse train with a high frequency are present. By means of the manner of combination mentioned above, an optimum effect is achieved for each of the three associated therapies, and the therapies are influenced by one another to a minimal degree. In this embodiment each electrode can thus indicate one of eight activation combinations with the code word. This makes a wide application of the method (and the associated apparatus) possible.

It is preferable for the first and the second pulse train to be selected in such a way that the second frequency of the second pulse train is an integral multiple of the first frequency of the first pulse train. As a result, not only can the implementation be considerably simplified (both hardware and software), but it also makes it possible (as will be explained below) to prevent the convergence of pulses of a plurality of signal shapes for a plurality of electrodes, on account of which the mutual influence of the various signal shapes is further reduced.

It is preferable for a period of rest to be introduced after the first period, a DC signal with a DC value virtually equal to zero being assigned to the signal shape, and after the period of rest the first period and the period of rest are periodically repeated.

By making the signal shape virtually zero in a period of rest, it is not necessary for the patient or the medical staff to deactivate the apparatus after a certain time, but the treatment stops automatically. As a result, it is once again possible to prevent errors, and periodic interventions to switch the apparatus on and off become superfluous. In addition, this benefits the service life of the battery. As will be evident below, this period of rest also allows a so-called "therapy multiplex" to be used, as will be explained below.

The invention likewise provides a method of generating a group of signal shapes from an electro-stimulation signal to be provided at the same time to a plurality of electrodes for healing wounds by electro-stimulation, which comprises the following steps:

f) checking whether a first electrode is connected to the signal shape generator, and if the first electrode is connected, generating a first signal shape for the first electrode in a manner as described above;

g) repeatedly checking whether a further electrode is connected to the signal shape generator (23), and if the further electrode is connected, generating a further signal shape for the further electrode in a manner as described above, the duration of the first period, the duration of the first and the second period portion respectively and the duration of the first and the second, third and fourth period fractions respectively of the further signal shape being selected to be the same as those of the first signal shape;

h) checking, for each first period and period portion and period fraction of the signal shapes, whether a plurality of pulse trains occur simultaneously, and, if a plurality of pulse trains occur simultaneously, defining a shift for each pulse train of each signal shape in such a way that the pulses of the pulse trains do not overlap in time after shifting over the defined shifts, and associating the shifts with the period and period portion and period fractions with the simultaneous pulse train;

i) checking, for each first period and period portion and period fraction of the signal shapes, whether a plurality of DC signals occur simultaneously, and, if a plurality of DC signals occur simultaneously, calculating a first sum of the DC values of the DC signals occurring simultaneously, and if this first sum is greater than a first maximum value, calculating a first scale factor as a proportion of the first sum and the first maximum value, and associating the first scale factor with the period and period portion and period fraction with the simultaneous DC signal;

j) checking, for each first period and period portion and period fraction of the signal shapes, whether at least one DC signal and at least one pulse train occur simultaneously, and if at least one DC signal and at least one pulse train occur simultaneously, calculating a DC component of each simultaneous pulse train by multiplication of the pulse amplitude and the averaged duty cycle of the pulse train, and calculating a second sum of the DC values and the DC components of the simultaneously occurring DC signals and pulse trains, and, if the second sum is greater than a second maximum value, limiting the DC values which are greater than a limiting value to the limiting value, and associating the limiting value to the period and period portion and period fraction with the simultaneous DC signal, and recalculating the second sum this time taking into consideration the limited DC values, and, if the recalculated second sum is greater than the second maximum value, calculating a second scale factor as a proportion of the recalculated second sum and the second maximum value, and associating the second scale factor with the period and period portion and period fraction with the simultaneously occurring DC value or pulse train;

k) repeating the steps g) to j) inclusive for each further electrode, and adding the further signal shape to the group;

m) checking, for each first period and period portion and period fraction of the signal shapes, whether at least one shift or at least one limiting value or at least one scale factor is associated with the first period and period portion and period fraction, and, if at least one shift or limiting value or scale factor is associated, adapting the signal shapes of the group in each first period and period portion and period fraction, by checking whether the shift is associated with the first period or period portion or period fraction, and, if the shift is associated, shifting the pulse train over the associated shift, and by checking whether the limiting value is associated with the first period or period portion or period fraction, and, if the limiting value is associated, limiting the DC values greater than the limiting value, and by checking whether the first scale factor is associated with the first period or period portion or period fraction, and, if the first scale factor is associated, scaling the DC values with the first scale factor, and by checking whether the second scale factor is associated with the first period or period portion or period fraction, and, if the second scale factor is associated, scaling the limited DC values and the pulse amplitudes with the second scale factor.

The expression "simultaneous occurrence" of two pulse trains is intended to mean the entire pulse train, not simply the individual pulses. By way of example, if the first signal shape is a pulse train of 5 Hz in the first period, and the second signal shape has a first period portion with a DC signal, and a second period portion with a pulse train of 5 Hz, then the pulse trains "occur simultaneously" in the second period portion.

The expression "duty cycle" is intended to mean the pulse width multiplied by the frequency.

The expression "averaged duty cycle" is intended to mean the averaged pulse width multiplied by the frequency. This can occur for example when the pulse width of a pulse train is not constant, but for example assumes a variable value (for example alternating between 1 ms and 2 ms).

By forming the signal shapes as described above and by subsequently scaling and shifting them as described above, it is possible for a group of signal shapes to be generated for a plurality of electrodes. In this way, each wound has generated for it a signal shape which is adapted in an optimum manner to the desired therapeutic treatments of the wound, and, in addition, the method ensures that the therapies of the wounds influence one another as little as possible. This last is particularly important since the body is not a homogeneous conductor, and the actual current paths are not predictable.

The major advantage of this method is that the nurse merely has to select the electrodes which correspond to the desired therapy or therapies for each wound separately, and he or she only has to attach the electrodes to the apparatus, without any setting. The apparatus calculates all the settings itself, as a result of which human error in the setting of the parameters for the different signals is prevented to a maximum degree. In addition, it is immaterial which electrode is connected to which port of the apparatus, and the wrong wave shape on the wrong electrode cannot be provided by incorrect settings, in other words the possibility of confusing different signal shapes in the case of a plurality of electrodes is eliminated.

It has also been found that because of the scaling of the amplitudes and the shifting of the pulses the positioning of the electrodes on the body is less critical. After all, the body is not a homogeneous conductor, and this results in a complicated interaction of the various signals which is not simple to model. Because of the scaling and shifting, the signal shapes and the interaction thereof will always fall within therapeutic limits, even in the case of worst-case positioning of the electrodes (i.e. if all the currents of the various signals were to be added up together).

By reducing the DC signals with a value greater than the limit value to the limit value, it can happen for example that a plurality of DC signals with a small DC value (for example 100 μA) are scaled on account of one DC signal with a large DC value (for example 400 μA).

The method of generating the group of signal shapes optionally comprises additional steps, in which
in step h) a further test is made into whether the defined shift is greater than a maximum shift defined previously,
and in which in step i) a further test is made into whether the DC value scaled with the first scale factor of at least one signal shape is smaller than a first minimum value;
and in which in step j) a further test is made into whether the pulse amplitude scaled with the second scale factor of at least one signal shape is smaller than a second minimum value;
and if one of these tests is met, removing at least one signal shape from the first group, and recalculating the signals of the first group, and forming a second group as described above for the remaining signal shapes,
and in which the signal shapes of the first and the second group are shifted with respect to one another in such a way that the signal shapes of the first group are active in a first active period in which the signal shapes of the second group are at rest, and in which the signal shapes of the second group are active in a second active period which does not overlap with the first active period and in which the signal shapes of the first group are at rest.

If a large number (for example six or eight or ten or twelve or twenty or more) electrodes are connected to the same apparatus, and in a manner dependent upon the selected therapies, it is not always possible to find a shift which falls within the time available (of the duration of one period of the pulse train), or, if the scaling possibly delivers such small signals that the therapeutic effect is insufficient, then in that case a plurality of groups of signal shapes are produced which are provided in order to be activated in separate active periods, for example one after the other, which is called "therapy multiplex" in this patent publication.

The invention likewise relates to an assembly for healing wounds by electro-stimulation, comprising:
at least one electrode which comprises an encoding member in which a code word has been saved, the code word comprising at least two code word portions, and the first and the second code word portion identifies a first and a second therapeutic treatment respectively, and the first and the second code word portion have coupled to them a first and a second indicator respectively which indicate whether the therapeutic treatment associated with the code word portion in question should be activated or not;
an electronic apparatus with at least one port for connecting the apparatus to the electrode,
and with a data-processing unit connected to the port for retrieving the code word from the encoding member, and for defining the associated therapeutic treatments on the basis of the code word portions and for checking the activation of the indicators,
and with a signal shape generator with a memory for retrieving a first and a second signal associated with the first and the second therapeutic treatment respectively, and with a buffer for the formation and the further formation of a temporary signal shape.

The assembly with this electronic apparatus and this electrode can be used for performing a combined therapy on one or more wounds at the same time, it being unnecessary for the nursing staff to carry out any settings, merely to select the correct electrode on the basis of the therapeutic treatments, and to connect it to the apparatus, and the apparatus defines all the signal parameters itself on the basis of the indicators in the encoding member.

BRIEF DESCRIPTION OF THE FIGURES

The invention is further explained with reference to the following description and the accompanying figures. It should be noted that the figures are not necessarily drawn to scale (in particular the time axis), and that the proportions of the parts do not necessarily correspond to reality. The figures are used to describe the principles of the invention. The same elements are numbered in the same way throughout the different drawings.

FIGS. 11A-11D show in a diagrammatic manner how the temporary signal shape in the periods, period portions and period fractions of FIG. 10 can be defined on the basis of parameters;

FIG. 16 shows a signal shape as a function of time, in accordance with signal type T2 of FIG. 9;

FIG. 19 shows in detail part of FIG. 18 as a function of time;

FIGS. 21A and 21B show two signal shapes of a first and a second electrode of the same group; the two signal shapes corresponding to signal type T8 of FIG. 9, but the signal shape of FIG. 21B being shifted in time;

DETAILED DESCRIPTION OF PREFERRED EMBODIMENTS OF THE INVENTION

Figure 1:
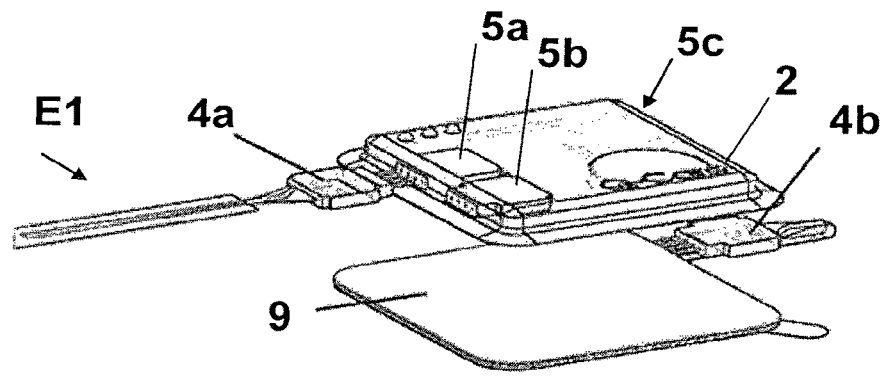
FIG. 1 is a diagrammatic illustration of a possible embodiment of an assembly according to the invention, with an electronic apparatus and an electrode.

The present invention will be described with respect to certain embodiments and with reference to certain drawings, but the invention is not limited to these and is defined solely by the claims. The drawings described are solely diagrammatic and non-limiting. In the drawings the size of certain elements may be exaggerated and not drawn to scale for illustrative purposes. The dimensions and the relative dimensions do not necessarily correspond to actual practical embodiments of the invention.

In addition, the terms "first", "second", "third" and the like in the description and in the claims are used in order to differentiate between similar elements and not necessarily to describe a sequential or chronological order. The terms are interchangeable with one another in appropriate cases and the embodiments of the invention can be applied in sequences other than those described or illustrated here.

The term "comprising", used in the claims, should not be interpreted as being limited to the means mentioned hereinafter and does not exclude other elements or steps. The term should be interpreted as specifying the presence of the named features, elements, steps or components to which reference is made, but does not exclude the presence or the addition of one or more other features, elements, steps or components, or groups thereof. The range of the expression "a device comprising means A and B" should not be restricted to devices which comprise only components A and B. It means that with respect to the present invention the relevant components of the device are A and B.

REFERENCES 1 assembly
2 electronic apparatus
3 data-processing unit
4 connector
5 port
6 encoding member
7 wire jumper
8 pin
9 central contact
10 gauze
11 rectangular part
12 ribbon-shaped part
13 optional connection
14 insulated electric wire
17 layer of silver
18 connector
19 hydrogel
20 plastics material sheet
21 user interface module
23 signal shape generator
24 feed module
25 connection module
31 operational amplifier
32 first diode
33 second diode
34 first connection pole 35 second connection pole
36 battery
37 micro-current module
38 memory element
E1 first electrode
i1 first indicator
w1 first signal shape (for first electrode)
cw code word
c1 first code word portion
α first scale factor
β second scale factor
Σ1 first sum
Σ2 second sum
Σ2' recalculated second sum
Tact1 first duration of time
Trust period of rest
d1 shift (of the first pulse train)
P1 first period portion
P1a first period fraction (of the first period portion)
P1b second period fraction (of the first period portion)
P2 second period portion
P2a first period fraction of the second period portion, third period fraction
P2b second period fraction of the second period portion, fourth period fraction
Ta duration of the first period fraction
Tb duration of the second period fraction
D1 first DC value
D1* reduced first DC value
PT1 first pulse train
f1 first frequency (of the first pulse train)
A1 first pulse amplitude (of the first pulse train)
B1 first pulse width (of the first pulse train)
PT2 second pulse train
f2 second frequency (of the second pulse train)
A2 second pulse amplitude (of the second pulse train)
B2 second pulse width (of the second pulse train)
T1 signal shape Type 1
G1 first group of signal shapes in the first active period The invention relates generally to the healing of wounds by micro-current therapy. More specifically, the invention relates to a method of generating a signal shape w1 which can be used in the production of micro-current signals, these being currents with an amplitude of less than 1 mA, which in turn can be applied to a wound by means of an electrode E1 to stimulate the healing of the wound. Currents of this type can be used for example for the treatment of chronic wounds such as bedsores, venous ulcers, diabetic foot, as well as in the case of burn wounds and internally, for example ruptures of the muscles, ligaments and tendons.

FIG. 1 shows an embodiment of an electronic apparatus 2 which comprises three ports 5a, 5b and 5c for receiving three connectors 4a, 4b, 4c. In this example the first connector 4a is part of a first electrode E1 which is shown only in part. A second electrode E2 (not shown) can be connected to the apparatus 2 by way of the second port 5b. The third port 5c is provided in order to be connected to a central contact 9 which is preferably positioned under the apparatus 2 for contact with the skin. The central contact 9 is used as a return channel of one or more micro-currents which are applied to the one or more electrodes E1, E2. The connector 4c of the central contact 9 is preferably physically different (for example wider or narrower) than the connectors 4a, 4b of the actual electrodes E1, E2, in order to minimize the possibility of incorrect attachment, whilst the connectors 4a, 4b of the electrodes E1, E2, which are provided in order to be positioned on or in wounds, preferably have the same physical dimensions.

Figure 2:
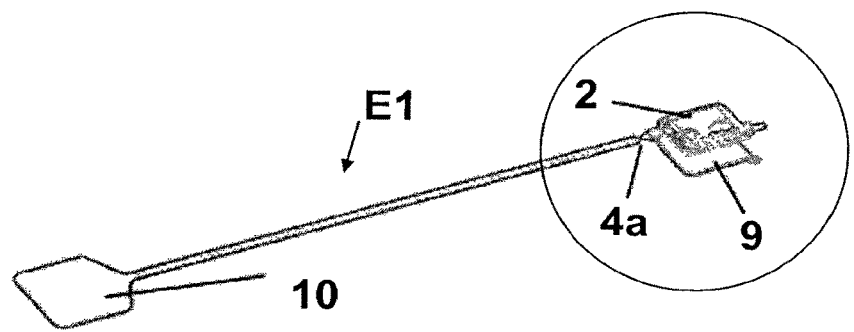
FIG. 2 is a diagrammatic illustration of a possible design of the electronic apparatus with a central contact below the apparatus and one electrode for on the wound.

FIG. 2 shows the apparatus 2 and the electrode E1 of FIG. 1 from a greater distance, in which the other tip of the electrode E1 is now also visible, where the electrode E1 opens into an electrically conductive gauze 10 which in this case has a pentagonal shape which can be attached to or in the wound. Electrodes with a conductive gauze are known in the prior art. What is characteristic of the electrode E1 belonging to the apparatus 2 is that it is connected to an encoding member 6 which comprises a code word cw which indicates which therapeutic treatment or treatments should be carried out on the wound in question, so that the electronic apparatus 2 can produce a suitable current signal for electro-stimulation. An aim of the invention is to define a signal shape w1 from which the suitable current signal can be derived. The encoding member 6 can be a part of the electrode E1, but it can also be for example a separate circuit which is connected between a port of the electronic appliance and the connector of the electrode. It is preferable for the encoding member 6 to be incorporated in the connector 4 of the electrode E1 and not capable of being changed or set by the patient or the nurse. It is preferable for the code word cw to be fixed during the production of the electrode E1. During the production of the electrode E1 it is thus determined which therapies will be subsequently carried out with this electrode, and it is the task of the nurse to select the correct electrode in a manner dependent upon the requirements, and it is the task of the apparatus 2 to generate a suitable signal shape which best meets one or more therapies to be activated.

Figure 25:
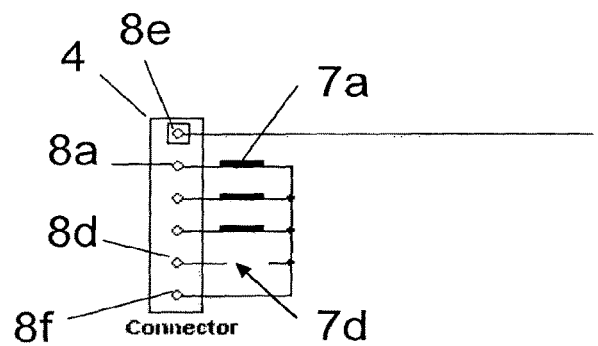
FIG. 25 shows an example of a connector with wire jumpers, as an embodiment of the encoding member connected to the electrode.

FIG. 25 shows an example of a connector 4 with wire jumpers 7 as a possible form of the encoding member 6. This connector has six pins 8, one pin of which (for example the uppermost pin 8e in FIG. 25) is used for transmitting the micro-current for the electrotherapy, and one pin of which (for example the lowest pin 8f in FIG. 25) is used for applying a test voltage in order to read out the code word cw. In this case the code word cw is formed by the position of the four remaining pins 8a to 8d, which form four code word portions c1 to c4, and identify the four therapeutic treatments tb1 to tb4 (for example in this case four therapeutic treatments selected in advance) which are encoded in a fixed manner in the apparatus (hard-coded). Each code word portion c1 to c4 has coupled to it an indicator i1 to i4 which indicates whether the related therapeutic treatment tb1 to tb4 has to be activated or not. In the example of FIG. 25 the value of each indicator i1 to i4 is determined during the production by the positioning or non-positioning of a connection 7 between the pin 8a to 8d of the connector and the test pin (pin 8f at the bottom of FIG. 25). In the example of FIG. 25 the first three indicators i1 to i3 indicate activation, i.e. the first, second and third therapies have to be activated, since a wire jumper 7 (or a zero-ohm resistor or the like) is provided. In this patent publication the formulation that the indicator has "yes" is intended to mean that it "indicates activation", and "no" that it indicates no activation. The fourth indicator i4 is not true, which indicates that the fourth therapy should not be activated.

Figure 26:
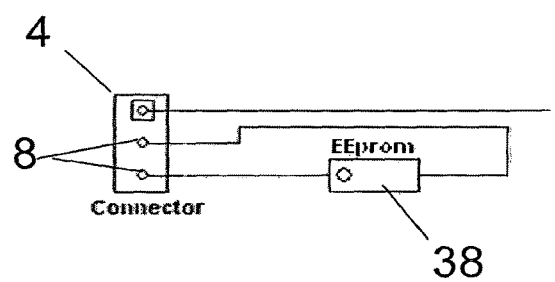
FIG. 26 shows an example of a connector with a memory element, as an embodiment of the encoding member connected to the electrode.

FIG. 26 shows an example of a connector 4 with a serial EEPROM as a possible form of encoding member 6. In this example a 2-pin component ("single-wire EEPROM") is used for stocking the code word cw. The code word cw can in turn comprise a plurality of code word portions c1 to c4 (but the number of code word portions can also be two or three or another number, for example six or eight or ten), in which each memory location (address) identifies a previously defined therapeutic treatment tb1 to tb4, and in which the content of the memory location reproduces the value of the indicator i1 to i4 coupled to it. The commercially available component DS2431 of Maxim® can serve as an example. This has a memory of 4×256 bits, but other memories such as flash can also be used. In principle, 4 bits are sufficient for the value of the indicators i1 to i4. Where appropriate the other memory locations of the electronic component can be used in order to save the associated base signals s1 to s4 belonging to the therapies. These base signals to s4 are preferably signals capable of being parameterized, such as a DC signal with a DC value D, or a pulse train with a frequency f and a pulse amplitude A and a pulse width B, and the value of the parameters D, f, A and B can be saved in the memory. Alternatively, these parameters can also be saved in an internal memory of the electronic apparatus 2. Other information is also optionally saved in the memory 38 of the electrode, such as manufacturing information (for example batch number, date of production), storage life and validity of the electrode E1.

As well as the examples of FIG. 25 and FIG. 26 it is also possible for another electronic or mechanical encoding of the connector 4 to be used, which can be recognized by the apparatus 2, for example by the activation of micro-switches (not shown). The assisted therapies tb1 to tb4 of an assembly 1 comprising an electronic apparatus 2 and one or more electrodes E1 are usually fixed and baked in (for example hard-coded) beforehand in the apparatus 2, so that only the value of the indicators has to be saved in the connector 4, each code word portion c1 to c4 for example corresponding to a fixed pin number or a fixed memory address.

Figure 3:
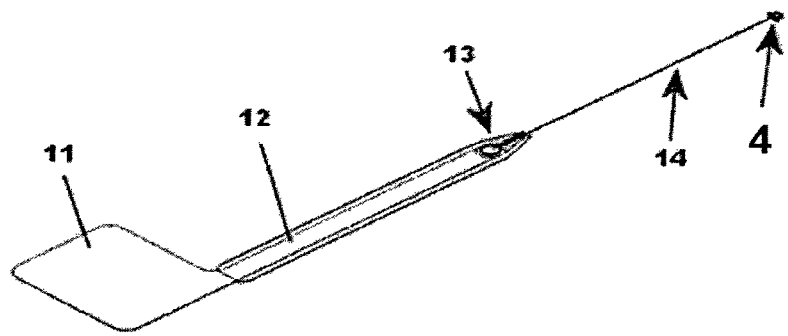
FIG. 3 is a diagrammatic illustration of a possible design of an electrode provided to be positioned on the wound.
Figure 4:
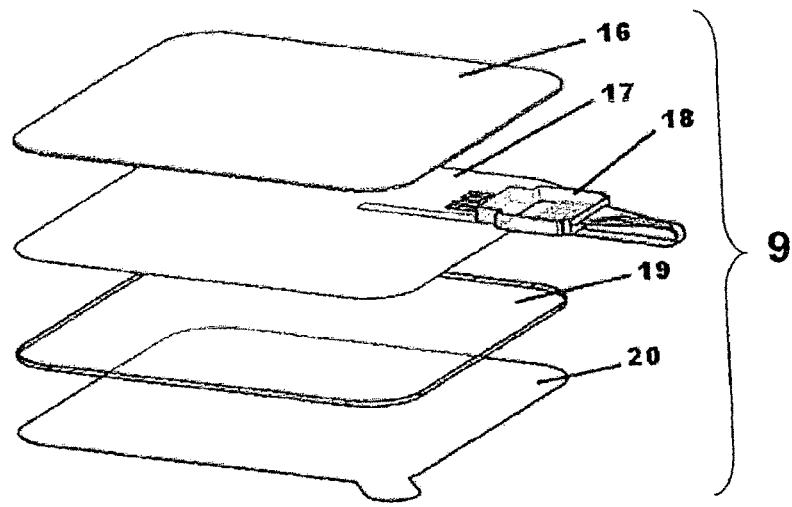
FIG. 4 is a diagrammatic illustration of a possible design of a central contact outside the wound.
Figure 5:
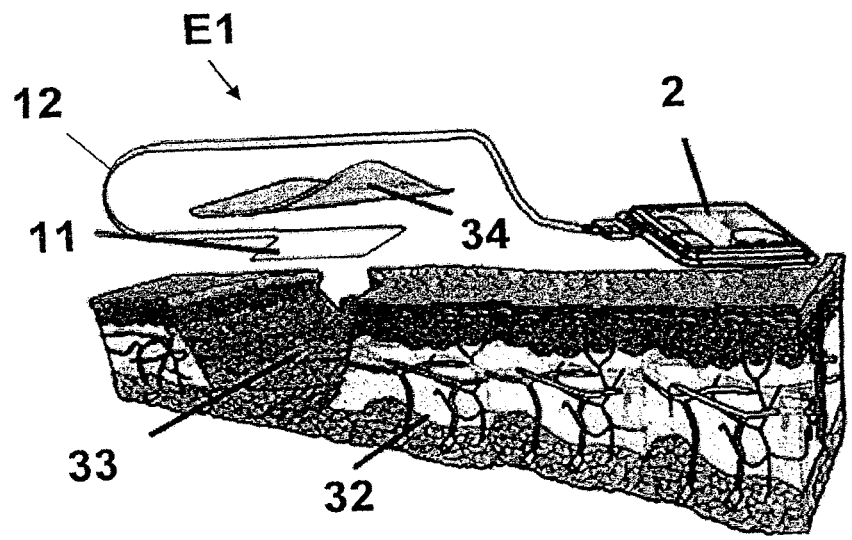
FIG. 5 shows an example of a possible positioning of an electrode with regard to the wound; with regard to the bandages and with regard to the electronic apparatus.

Before describing in detail the method of generating the signal shapes, FIGS. 3 to 5 are first discussed in order to explain the application of the invention further.

FIG. 3 shows an embodiment of an electrode E1 suitable to be attached to a wound. The rectangular part 11 of the electrode E1 in a nylon gauze with a layer of silver is for direct contact with the wound bed, the ribbon-shaped part 12 of the same material is used to produce an electrically conductive pad without the risk of softening the edge of the wound or pressure injury, and an optimum connection 13 to an insulated electrical wire 14 affords the possibility of a more distant connection by way of the connector 4 to the electronic apparatus 2.

Metal ions can be released under the influence of an electrical potential. In order that the electrode on the wound should contain silver (or another metal), the central contact 9 of the apparatus 2 is preferably kept at a positive potential (anode) with respect to the electrode on the wound during the stimulation (cathode). In this way, discharges of metal onto the body (in the form of ions or colloidally) is limited and interaction with medical products is minimized. In contrast to other solutions the electrode on the wound is not dedicated to the discharge of ions, so that the electrode on the wound can remain active for a number of days in order not to disturb the wound bed and the conventional therapy.

FIG. 4 shows an embodiment of a central contact 9 or a tip of an electrode E1 outside the wound. In the case of a supporting central contact the electrically insulating uppermost layer 16 can be provided on the top side of a double-adhesive layer, A layer of silver 17 ensures a uniform distribution of the current density over the surface of the central contact. The connector 18 with a wire connection is intended to be connected to the electronic apparatus 2. The hydrogel 19 makes the physical and electrical connection to the skin. A protective plastics material film 20 is provided in order to protect the hydrogel from harm, UV damage and dehydration during the transport and saving.

FIG. 5 shows an example of a possible positioning of an electrode E1 with respect to a wound, with respect to bandages and with respect to the electronic apparatus 2. The skin 32 is illustrated in the form of a cross-section with an open wound and the wound bed 33. The optimum positioning of the electrode E1 is such that the ribbon-shaped part 12 leaves the wound or edge of the wound at the furthest possible position with respect to the electronic apparatus 2. The gauze 11 of the electrode E1 is preferably covered by conventional wound bandages 34 and the ribbon-shaped part 12 of the electrode E1 is preferably laid over the bandages. In this way, a further attempt is made towards an optimum distribution of the current density in the wound bed, in order that the flow paths are positioned to the maximum degree through the wound and the non-homogeneous character of the conduction in the body is minimized.

Figure 6:
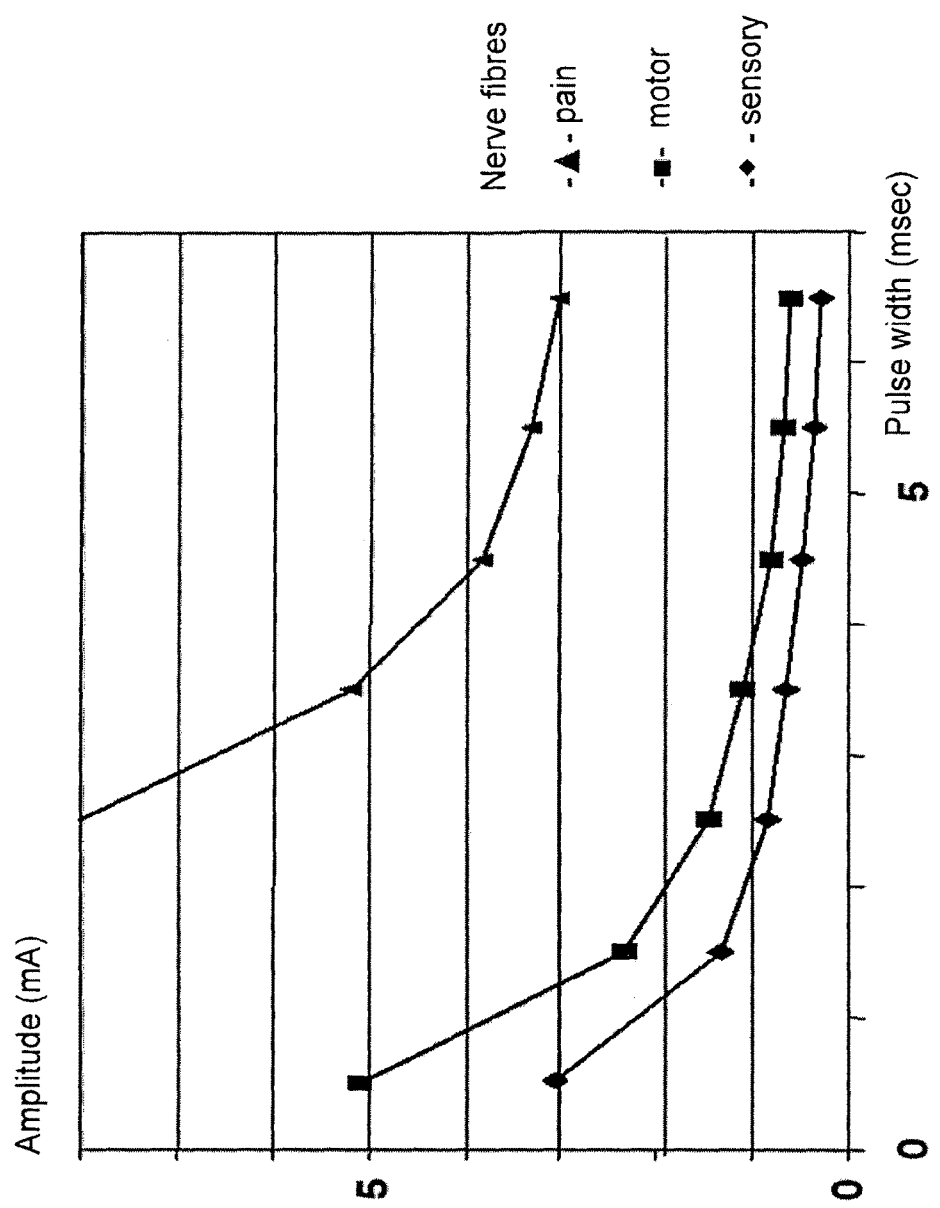
FIG. 6 shows the individual graphs from the prior art of the pulse amplitude against the pulse width for the stimulation of the various nerve systems.

FIG. 6 shows separate graphs from the prior art. The lowest curve (with diamonds) shows the maximum permitted pulse amplitude A of a pulse train PT as a function of the pulse width B in such a way that the sensory nerves are not excited. The method according to the present invention provides a signal shape which always remains below this curve, in other words this known curve is used as a boundary condition.

Figure 7:
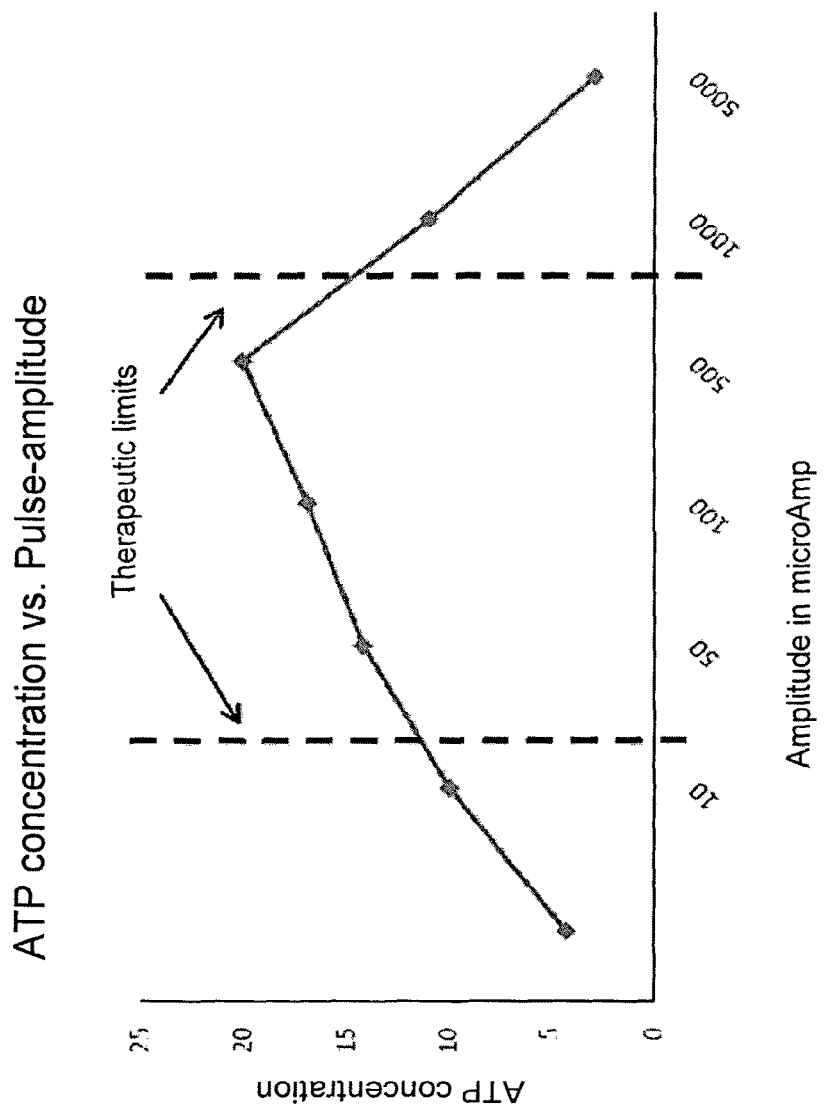
FIG. 7 shows a graph from the prior art which indicates an increase in the ATP concentration as a function of the pulse amplitude of a pulse train in animal tissue.

FIG. 7 shows another graph from the prior art which indicates a typical increase of ATP concentration in the case of electro-stimulation, as a function of the pulse amplitude A of a pulse train PT. It has been shown in tests that the exact curves are linked to the person. The graph also shows that the ATP concentration sharply drops when the pulse amplitude A is too great (for example greater than 1000 µA). The inventor has indicated therapeutic limits to this figure, i.e. a minimum amplitude of approximately 25 µA, and a maximum amplitude of approximately 750 µA, within which the signal shape w1 which is used to stimulate ATP production should remain, as will be described below. The existing curves from the prior art are thus regarded as being boundary conditions.

Figure 8:
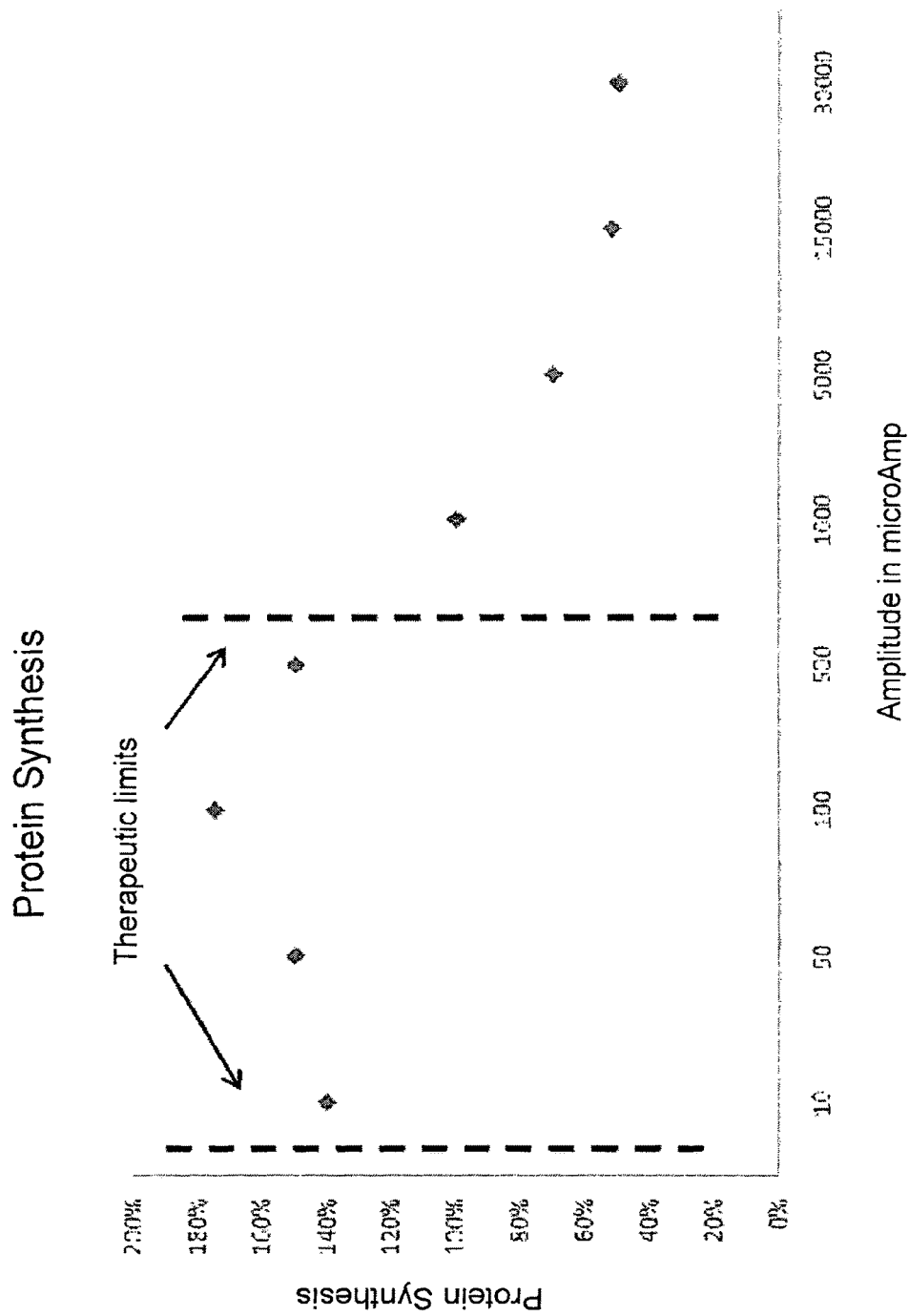
FIG. 8 shows a graph from the prior art which reproduces protein production as a function of the pulse amplitude of a pulse train.

FIG. 8 shows another graph from the prior art which indicates a typical increase of protein production in the case of electro-stimulation, as a function of the pulse amplitude A of a pulse train PT. For this therapeutic treatment use can therefore best be made of a pulse train of which the amplitude is a value between for example 10 and 750 µA, which are indicated as therapeutic limits for this treatment, and which are in turn regarded as being boundary conditions.

FIGS. 6 to 8 show some examples of therapeutic limits which a micro-current pulse train has to meet in order to achieve certain therapeutic effects such as the increase of ATP concentration or protein production (FIGS. 7 and 8), or the prevention of undesired effects such as perceptible nerve stimuli (FIG. 6). By way of graphs of this type the inventor has defined boundary conditions which should be observed by the signal shapes w1, w2 which will be generated.

Example of an Apparatus with Two Ports, and with Four Code Word Portions

The invention will be further explained in detail with reference to a specific example, as well as the preferred embodiment of a method and an apparatus 2 according to the invention, in which the apparatus 2 has two ports 5a, 5b to which two electrodes E1, E2 can be connected at the same time, each electrode E1, E2 having an encoding member 6a, 6b, preferably incorporated in the connector 4a, 4b of the electrodes E1, E2 and each encoding member 6a, 6b containing a code word cw1, cw2 which both contain four code word portions c1 to c4, this relationship between the code word portion and the corresponding therapeutic treatment being reproduced in Table 1.

TABLE 1

| code word portion | associated therapeutic treatment | associated base signal |
|---|---|---|
| c1 | tb1: antibacterial treatment | s1 |
| c2 | tb2: cell migration treatment | s2 |
| c3 | tb3: treatment for pain and/or a treatment for the increase in the oxygen tension TcPO2 | s3 |
| c4 | tb4: stimulation of one or more processes chosen from the group of: ATP production, DNA production, protein production and amino acid absorption | s4 |

Although the invention will be described primarily with reference to this specific example, it is obvious to the person skilled in the art that a variant of the apparatus 2 described can contain only one port 5 or more than two ports 5 for connecting more than two electrodes, for example, 3 or 4 or 6 or 8 or 10 or even more. It is also obvious to the person skilled in the art that a variant of the apparatus 2 can support less than four or more than four therapeutic treatments, for example two or three or five or six or more.

The encoding member 6 further comprises, for each of the code word portions c1 to c4, an indicator i1 to i4 which indicates whether the therapeutic treatment in question has to be activated or not. In the preferred embodiment of the invention the therapeutic treatments have been selected in advance and hard-coded (baked in) into the hardware and/or the software of the electronic appliance, or saved in an internal memory, and the values of the indicators i1 to i4 are fixed during the production of the electrodes E1, E2. The nurse thus merely has to chose a suitable electrode for each wound in accordance with the desired therapeutic treatments for the wound in question. A data-processing unit 3 (for example a micro-processor) of the apparatus 2 will then read out the value of the indicators saved in the respective electrode by way of the port or ports 5 of the apparatus 2, and will generate a suitable signal shape w1, w2 for each of the electrodes E1, E2 in a manner dependent upon the indicators.

Figure 12:
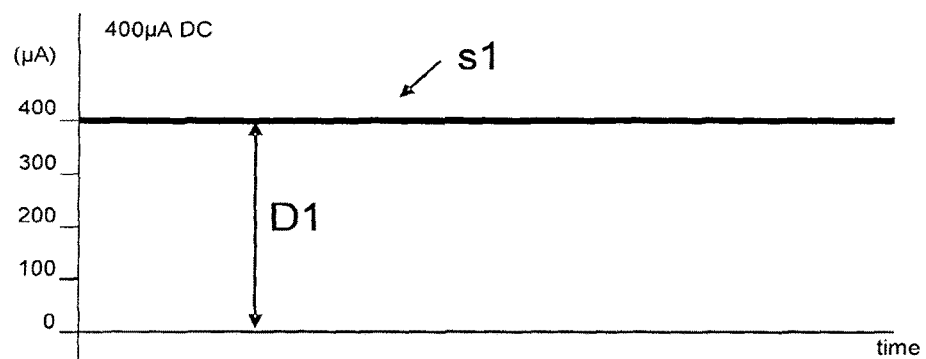
FIG. 12 shows a first DC signal, as well as a first base signal in the preferred embodiment of the method according to the invention.

In the preferred embodiment of the method according to the invention an associated signal s1 to s4 is chosen for each of the therapeutic treatments of Table 1, as follows:

In accordance with an antibacterial treatment a DC signal is preferably chosen with a first DC value D1 of from 4 to 750 μA, preferably from 300 to 500 μA, more preferably approximately 400 μA, as shown in FIG. 12. This is the first base signal s1 in the preferred embodiment.

It has been shown in studies that a negative DC current in the order of from 4 to 400 μA (microamps) in the wound bed has a bacteriostatic and an antibacterial effect.

Figure 13:
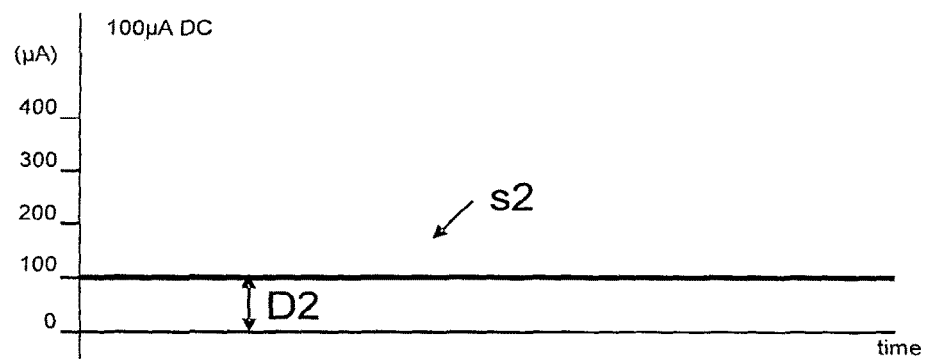
FIG. 13 shows a second DC signal, as well as a second base signal in the preferred embodiment of the method according to the invention.

In accordance with a cell migration treatment a DC signal is preferably chosen with a second DC value D2 of from 50 to 750 μA, preferably approximately 100 μA, as shown in FIG. 13. This is the second base signal s2 in the preferred embodiment.

It has been shown in studies that a DC current of this type is the optimum in order to stimulate the migration of epithelia and fibroblasts, keratinocytes and neutrophils towards the wound bed (galvanotaxis).

Figure 14:
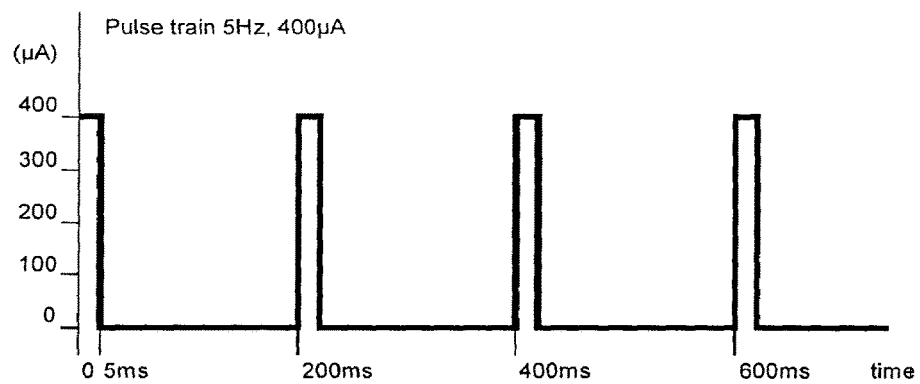
FIG. 14 shows a first pulse train, as well as a third base signal in the preferred embodiment of the method according to the invention.

In accordance with a treatment for pain and/or a treatment for the increase in the oxygen tension TcPO2 a first pulse train PT1 is preferably chosen with a first frequency f1 of from 0.2 to 20.0 Hz, preferably from 1.0 to 10.0 Hz, more preferably approximately 5.0 Hz, with a first pulse amplitude A1 of from 10 to 750 μA, preferably from 100 to 400 μA, for example 400 μA, and a first pulse width B1 of from 0.1 to 20 ms, preferably from 1.0 to 3.0 ms, for example 2 ms, as shown in FIG. 14. This is the third base signal s3 in the preferred embodiment.

A pulse frequency of from 0.2 to 20.0 Hz (typically 5.0 Hz) appears to be the optimum for pain control and the increase in TcPO2 (blood circulation of the skin, i.e. oxygen tension on the skin). A variation of the pulse width (for example in succession 1, 2, 2, 1 ms) is effective for stimulating nerves at different energy levels.

Figure 15:
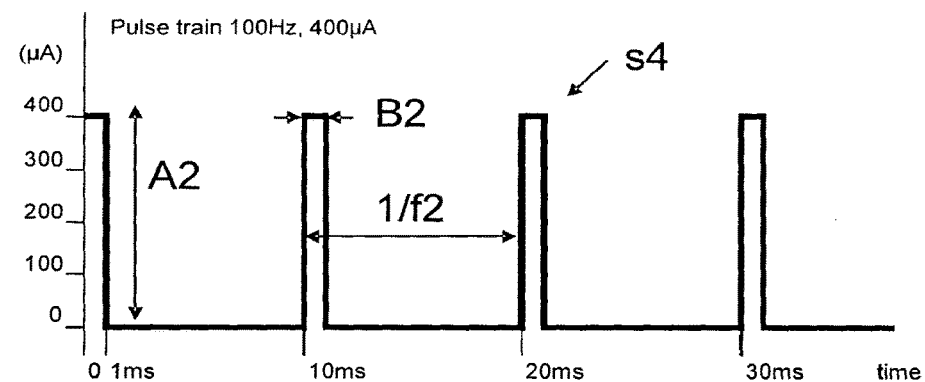

In accordance with stimulation of a process selected from the group of ATP production, DNA production, protein production and amino acid absorption, a second pulse train PT2 is preferably chosen with a second frequency f2 of from 50 to 160 Hz, preferably from 75 to 125 Hz, more preferably approximately 100 Hz, and a second pulse amplitude A2 of from 10 to 750 μA, preferably from 100 to 400 μA, for example 400 μA, and a second pulse width B2 of from 0.1 to 5.0 ms, preferably from 0.2 to 2.0 ms, for example 1.0 ms, as shown in FIG. 15. This is the fourth base signal s4 in the preferred embodiment.

A pulse frequency of from 50 to 160 Hz (typically 100 Hz) appears to be the optimum for stimulating the ATP, DNA and protein production and amino acid absorption, and for reducing the accumulation of moisture in the tissue, and, in addition, is more suitable for overcoming the higher impedance of the low-conducting skin transition. This pulse shape can also be used for testing the correct electrical connection (testing of error condition).

The method according to the invention will generate a signal shape w1 starting from these base signals s1 to s4, but in a manner which depends upon the therapies selected, as indicated by the indicators i1 to i4. The details of this method will be explained mainly with reference to FIGS. 9, 10 and 11A-11D.

Figure 9:
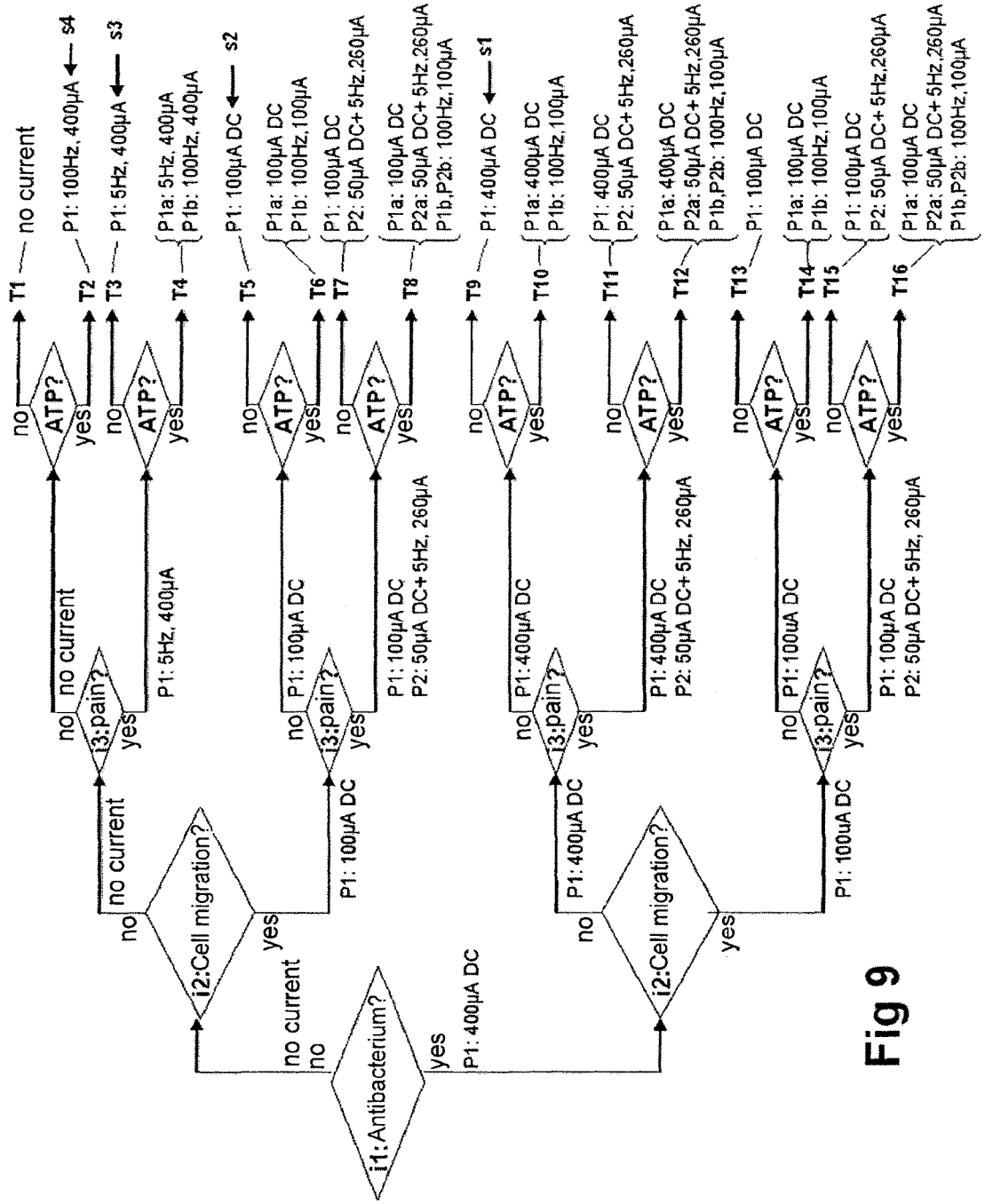
FIG. 9 shows a flow diagram of a preferred embodiment of the method according to the invention; with four code words.

FIG. 9 is a flow diagram of the preferred embodiment of the method according to the invention, with four code word portions c1 to c4 and four indicators i1 to i4 in accordance with Table 1. All possible combinations of "active" (J) and "non-active" (N) are illustrated. For the third indicator only "pain" is mentioned, and for the fourth indicator only "ATP" is mentioned, but a more complete description is given above in Table 1.

Only One Indicator Active:

Let us first consider the case in which only one indicator i1 to i4 is active. Let us suppose that only one electrode E1 is connected to the apparatus 2, and let us imagine that the data-processor unit (for example the micro-processor) 3 of the apparatus 2 has the following indicators: i1=yes, i2=no, i3=no, i4=no. The signal shape w1 is then generated as follows: First a check is made as to whether the first indicator indicates activation, and this is in fact the case in this example. The associated signal s1, in this case a DC signal with a DC value D1 of 400 μA (see FIG. 12), is saved, and a temporary signal shape w is formed on the basis of this first signal s1, for example by taking this first signal over a first period Tact1. It is preferable for the first period Tact1 to have a duration of approximately 90 minutes. After that, a check is made as to whether the indicators i2 to 14 indicate an activation, and this is not the case in this example, so that the temporary signal shape is retained and is not applied.

Figure 10:
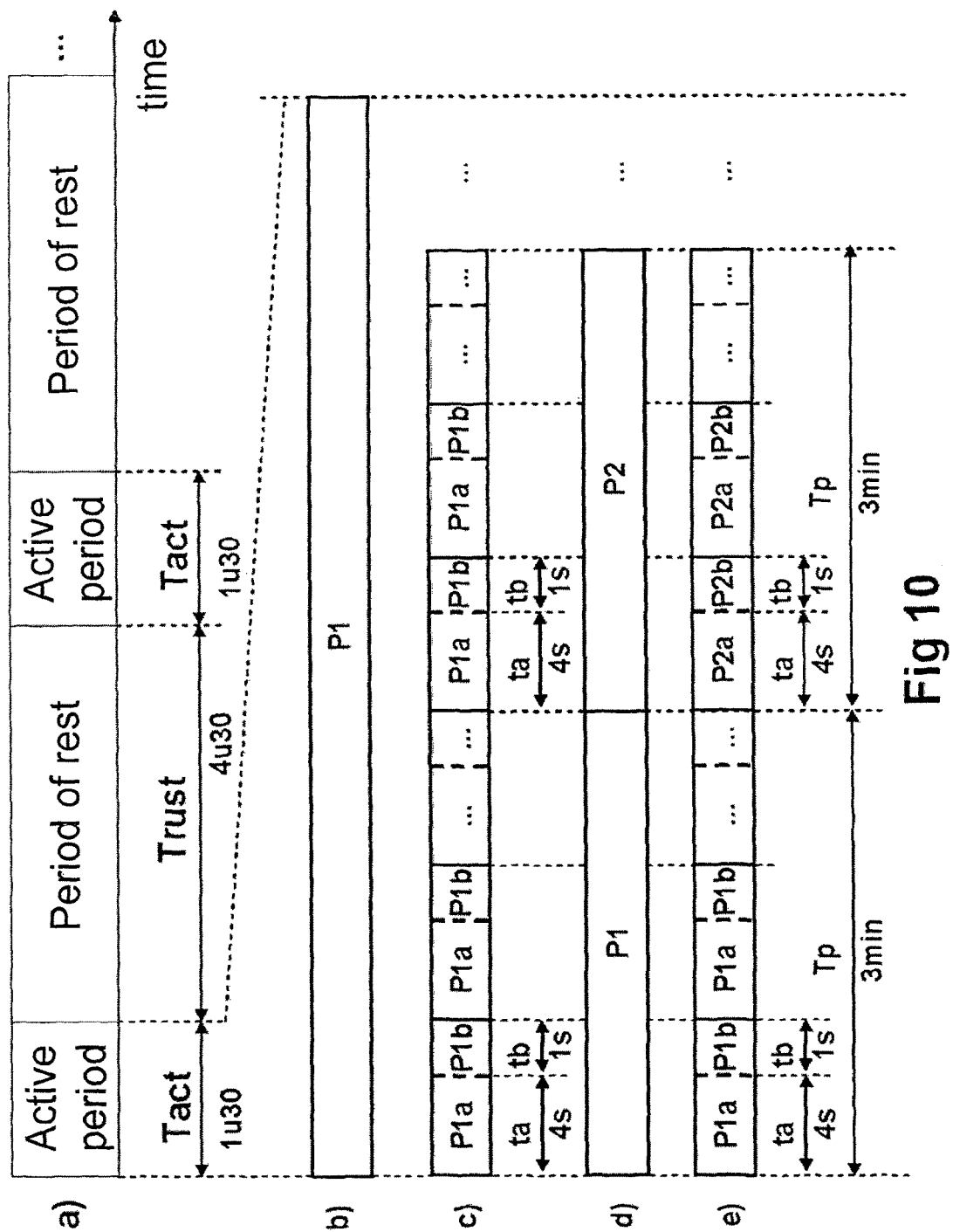
FIG. 10 is a timing diagram of the preferred embodiment of the method as shown in FIG. 9.

Finally, the signal shape w1 is generated with reference to the temporary signal shape w, in this case only s1, and that over the entire duration of the first period Tact. FIG. 10 reproduces the time aspect of the signal shapes w1 formed by the preferred embodiment of the method according to the present invention. FIG. 10A shows that the signal shape w1 for the electrode E1 is active during a first period Tact of for example 1 hour 30 minutes, and after that is virtually zero in the period of rest lasting a time Trust of for example 4 hours 30 minutes, after which the cycle is repeated. The signal shape w1, which corresponds to the indicators i1=yes, i2=no, i3=no, i4=no, is thus in accordance with the method according to the invention a DC signal of 400 μA during the entire first period Tact, the time aspect of which is reproduced in FIG. 10b. The first 90 minutes of the signal shape w1 for the case in which only i1 is active, is thus also reproduced in FIG. 12. This is signal type T9 of FIG. 9, with the timing of FIG. 10b.

In an implementation the temporary signal shape w can be for example a set of parameters which define both the time aspect (for example with reference to the timing of FIG. 10b) and the signal shape (for example s2) and the parameters of the signal shape (for example D1=100 μA), whilst the signal shape w1 to be generated is for example a time-discrete or time-continuous signal shape.

In a similar manner, FIG. 13 also reproduces the first 90 minutes of the signal shape w1 which is generated when the indicators i1 to i4 of the electrode E1 are equal to: i1=no, i2=yes, i3=no, i4=no. In this case a check is first made as to whether the first indicator i1 is activated, which is not the case. After that, the second indicator i2 is considered, and that is indeed activated, the second signal s2 is retrieved, and a temporary signal shape w is formed on the basis of the second signal (for example by recognizing the second signal s2 over a duration of the first period Tact1). After that, a check is made as to whether the third and fourth indicators i3, i4 indicate activation, but, in view of the fact this is not the case, the temporary signal shape w is retained and not applied. Finally, the signal shape w1 is formed on the basis of the temporary signal shape w. This for example describes signal type T5 of FIG. 9, with the timing of FIG. 10b.

In a similar manner, FIG. 14 also reproduces the first 90 minutes of the signal shape w1 which is generated when the indicators i1 to i4 of the electrode E1 are equal to: i1=no, i2=no, i3=yes, i4=no. This is signal type T3 of FIG. 9, with the timing of FIG. 10b.

Figure 16:
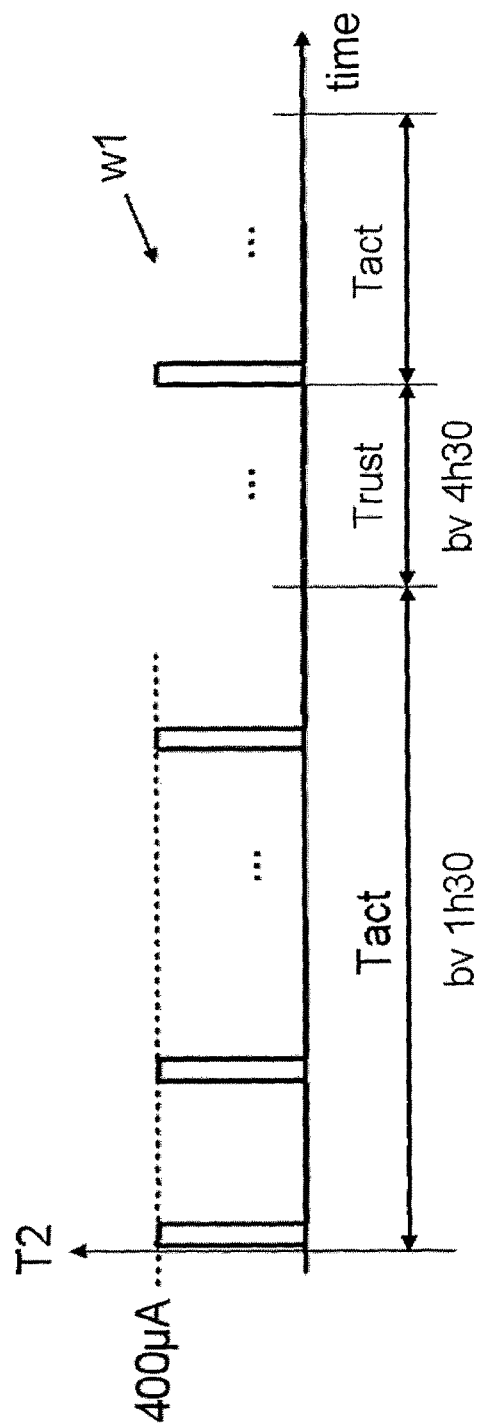
FIG. 16 shows a second pulse train, as well as a fourth base signal in the preferred embodiment of the method according to the invention.

In a similar manner, FIG. 15 also reproduces the first 90 minutes of the signal shape w1 which is generated when the indicators i1 to i4 of the electrode E1 are equal to: i1=no, i2=no, i3=no, i4=yes. This is signal type T2 of FIG. 9, with the timing of FIG. 10b, also reproduced in FIG. 16 (not to scale).

In view of the fact that only one therapy has to be activated in these four examples, it is not necessary to take into consideration another therapy, and in the cases mentioned above it is possible to go completely to the base signal s1, s2, s3, s4 associated with the therapeutic treatment to be activated.

Two Indicators Active at the Same Time

It becomes different when two or more indicators i1 to i4 are active at the same time, as the method according to the invention will then apply the temporary signal shape w (on the basis of the first signal s1) and combine it with the second signal s2. The algorithm will check all the code words and indicators, but only the most prominent steps are described in the description below, and so it is not always stated for example that a certain indicator is retrieved, the value of which was "no" and that the temporary signal shape already formed is retained.

For example, let us consider the example with i1=yes, i2=yes, i3=no, i4=no. The first indicator i1 indicates activation, and so the first signal s1, being a DC signal s1 with a first DC value D1=400 μA, is retrieved, and assigned to the temporary signal shape w. The second indicator i2 also indicates activation, and so the second signal s2, being a DC signal s2 with a second DC value D2=100 μA, is retrieved, and the temporary signal shape w (with s1 in it) is combined with the second signal s2, by the change from the DC value D1 to the smallest value of D1 and D2, being 100 μA. This is applied for example in signal type T13 of FIG. 9, with the timing of FIG. 10b.

Figure 17:
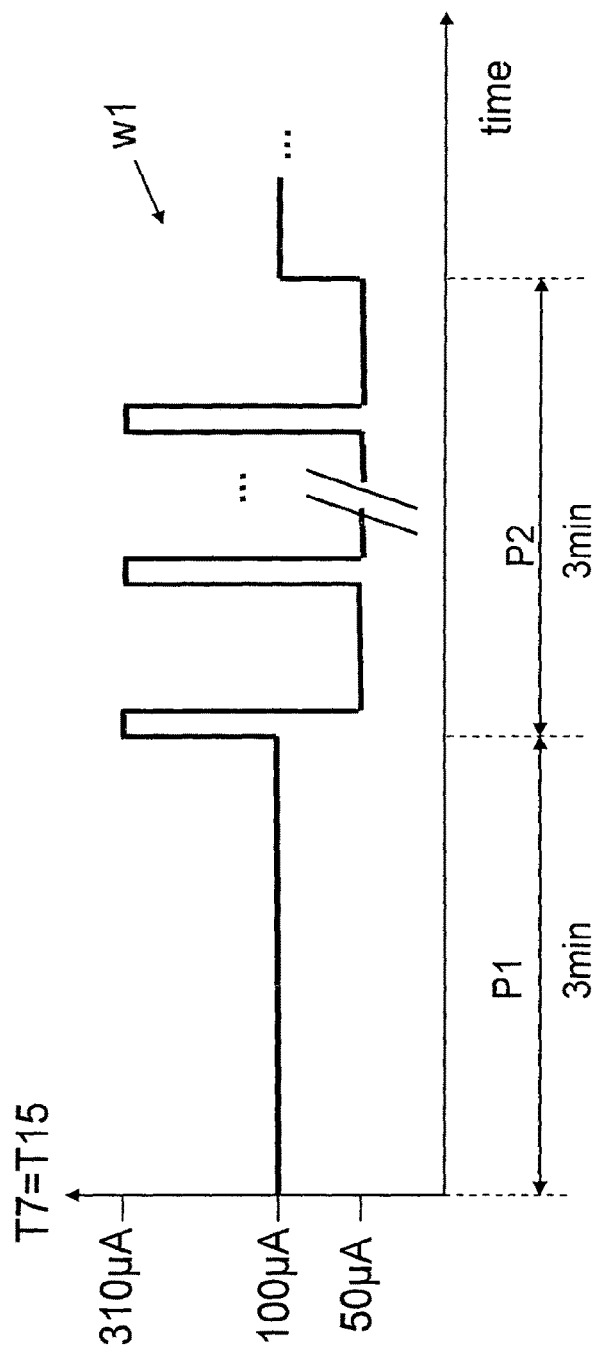
FIG. 17 shows a signal shape as a function of time, in accordance with signal type T7 and T15 of FIG. 9.

Let us consider the example with i1=no, i2=yes, i3=yes, i4=no. With the design of the temporary signal shape w the second signal s2, being a DC signal with a first DC value D1=100 μA, will be retrieved, and will be assigned to the temporary signal shape w. After that, the third signal s3 will be retrieved, being a first pulse train PT1 with a first frequency of 5 Hz and a first pulse amplitude A1=400 μA, which has to be combined with the temporary signal shape w. With the combination of a temporary signal shape which contains a DC signal, and a first pulse train PT1 with a frequency f1 lower than a previously defined frequency (for example 30 Hz), the first period Tact (for example 90 minutes) of the temporary signal shape w is split into at least one first and at least one second period portion P1, P2 (for example of 45 minutes each), the DC signal of 100 μA being retained in the at least one first period portion P1, and the first DC value D1 of 100 μA being reduced to a reduced DC value D1* of for example approximately 50 μA in the at least one second period portion P2, and the first pulse amplitude A1 (of 400 μA) being reduced to a reduced first pulse amplitude A1* of from 200 to 300 μA, for example approximately 260 μA, and the first pulse train PT1 with the reduced first pulse amplitude A1* is superimposed upon the first DC signal with the reduced DC value D1*. In other words, in the second period portion P2 the temporary signal shape w becomes a superimposition of 5 Hz pulses with a pulse amplitude of 260 μA on a DC value of 50 μA. This is applied for example in signal type T7 of FIG. 9, with the timing of FIG. 10d. A specific example of the signal shape of signal type T7 of FIG. 9 is reproduced in FIG. 17, in which a plurality of first and second period portions P1, P2 (for example of 3 minutes in each case) are selected, which occur alternately during the first period Tact1 (for example 90 minutes). The reasons for the reduction of the DC value D1 in the second period portion P2 lie in the polarization of the nerve endings on account of the DC value, the inventor having chosen in advance not to stimulate the sensory nerves.

It is preferable for each first and second period portion P1, P2 to have a duration of from 1 to 45 minutes, preferably a duration of from 1 to 20 minutes, and in a more preferred manner a duration of virtually 3 minutes. Such a duration provides a successful stimulation for different forms of therapy (in vitro, in vivo).

Let us consider the example with i1=yes, i2=no, i3=no, i4=yes. The temporary signal shape w is formed in the first instance on the basis of the first DC signal s1 with a first DC value D1=400 μA. After that, the fourth signal s4 is retrieved, being a second pulse train with a second frequency f2 of 100 Hz, and a second pulse amplitude of 400 μA. With the combination of the temporary signal shape w (with the first DC signal in it) and the second pulse train PT2, the first period Tact1 (for example 90 minutes) is split into a plurality of period portions P1 (for example 3 minutes each), and each period portion P1 is fractioned into a first and a second period fraction P1a, P1b, the DC signal with the first DC value D1 (of 400 µA) being retained in the first period fraction P1a, and the second pulse amplitude A2 (of 400 µA) being reduced to a reduced second pulse amplitude A2* (of 100 µA) in the second period fraction P1b, and the DC signal in the temporary signal shape w is replaced by the second pulse train PT2 with the reduced second pulse amplitude A2* (of 100 µA). This is applied for example in signal type T1 of FIG. 9, in which the first period fraction P1a has a DC value D1 of 400 µA, and in which the second period fraction P1b has a pulse train PT2 with a second frequency f2 of 100 Hz and a reduced pulse amplitude A2* of 100 µA.

It is preferable for each period portion P1 to be fractioned into a first period fraction P1a with a first fraction duration Ta and into a second period fraction P1b with a second fraction duration Tb, the ratio of the second fraction duration Tb and the first fraction duration Ta being a ratio of from 10/90 to 40/160, preferably approximately equal to 20/80. By way of example, the first fraction duration Ta is approximately equal to 4.0 seconds, and the second fraction duration Tb is approximately equal to 1.0 seconds.

The stimulation with the second pulse train PT2 with a "high" frequency has a positive therapeutic effect even after a short duration (for example after 1 to 10 minutes), but requires a lower dose for a fair result, and, in addition, is cumulative over separate periods. In this way, this stimulation can be applied briefly and repeatedly in terms of time, to the advantage of other forms which require longer administration.

Let us consider the example with i1=no, i2=no, i3=yes, i4=yes. The temporary signal shape w is formed on the basis of the first pulse train PT1 with a first frequency f1 of 5 Hz, and with a first pulse amplitude A1 of 400 µA and with a first pulse width B1 of 2.0 ms. After that, the fourth signal s4 is retrieved, being a second pulse train with a second frequency f2 of 100 Hz, and a second pulse amplitude of 400 µA. With the combination of the temporary signal shape w (with the first pulse train in it) and the second pulse train PT2, the first period Tact1 (for example 90 minutes) is split into a plurality of period portions P1 (for example 3 minutes each), and each period portion P1 is fractioned into one or more first period fractions and a second period fraction P1a, P1b, the first pulse train PT1 with the first pulse amplitude A1 (of 400 µA) being retained in the first period fraction P1a, and the first pulse train PT1 being replaced by the second pulse train PT2 in the second period fraction P1b. This is applied for example in signal type T4 of FIG. 9, with the timing of FIG. 10c. In this case the pulse amplitudes remain 400 µA both for the first pulse train PT1 of 5 Hz and for the second pulse train PT2 of 100 Hz. After all, no polarization of the nerve endings occurs in this case on account of a DC signal.

Three Indicators Active at the Same Time

Let us now consider the case in which three indicators are active at the same time, for example i1=yes, i2=no, i3=yes, i4=yes. The temporary signal shape w is formed on the basis of the DC signal s1 as described above. The second indicator i2 is "no", and so the temporary signal shape is retained. During the checking of the third indicator i3 the third signal s3 is retrieved, being a first pulse train PT1, which has to be assembled with the temporary signal shape w. For this, the first period Tact1 (for example 90 minutes) is split into at least one first and at least one second period portion P1, P2 (for example 45 minutes each), the first DC value D1 (for example 400 µA) being retained in the first period portion P1, and the first DC value D1 (of 400 µA) being reduced to a reduced DC value D1* (of 50 µA) in the second period portion P2, and the first pulse amplitude A1 (of 400 µA) being reduced to a reduced first pulse amplitude A1* (of 260 µA) and the first pulse train PT1 with the reduced first pulse amplitude A1* being superimposed upon the first DC signal with the reduced DC value D* (of 50 µA). During the checking of the fourth indicator i4 the fourth signal s4 is retrieved, being the second pulse train PT2, which has to be assembled with the temporary signal shape w already formed. For this, the first period portion P1 is fractioned into a plurality of first and second period fractions P1a, P1b, the DC signal with the first DC value D1 (of 400 µA) being retained in each first period fraction P1a, and the second pulse amplitude A2 (of 400 µA) is reduced to a reduced second pulse amplitude A2* (of 100 µA) in every second period fraction P1b, and the DC signal is replaced by the second pulse train PT2 with the reduced second pulse amplitude A2*. In addition, the second period portion P2 is also split into a plurality of third and fourth period fractions P2a, P2b, the DC signal with the reduced DC value D* (of 50 µA) with the first pulse train PT1 with the reduced first pulse amplitude A1* (of 260 µA) superimposed upon it being retained in each third period fraction P2a, and the second pulse amplitude A2 (of 400 µA) is reduced to a reduced second pulse amplitude A2* (of 100 µA) in each fourth period fraction P2b, and the DC signal with the reduced DC value D* with the first pulse train PT1 with the reduced first pulse amplitude A1* superimposed upon it is replaced by the second pulse train PT2 with the reduced second pulse amplitude A2* (of 100 µA).

Figure 18:
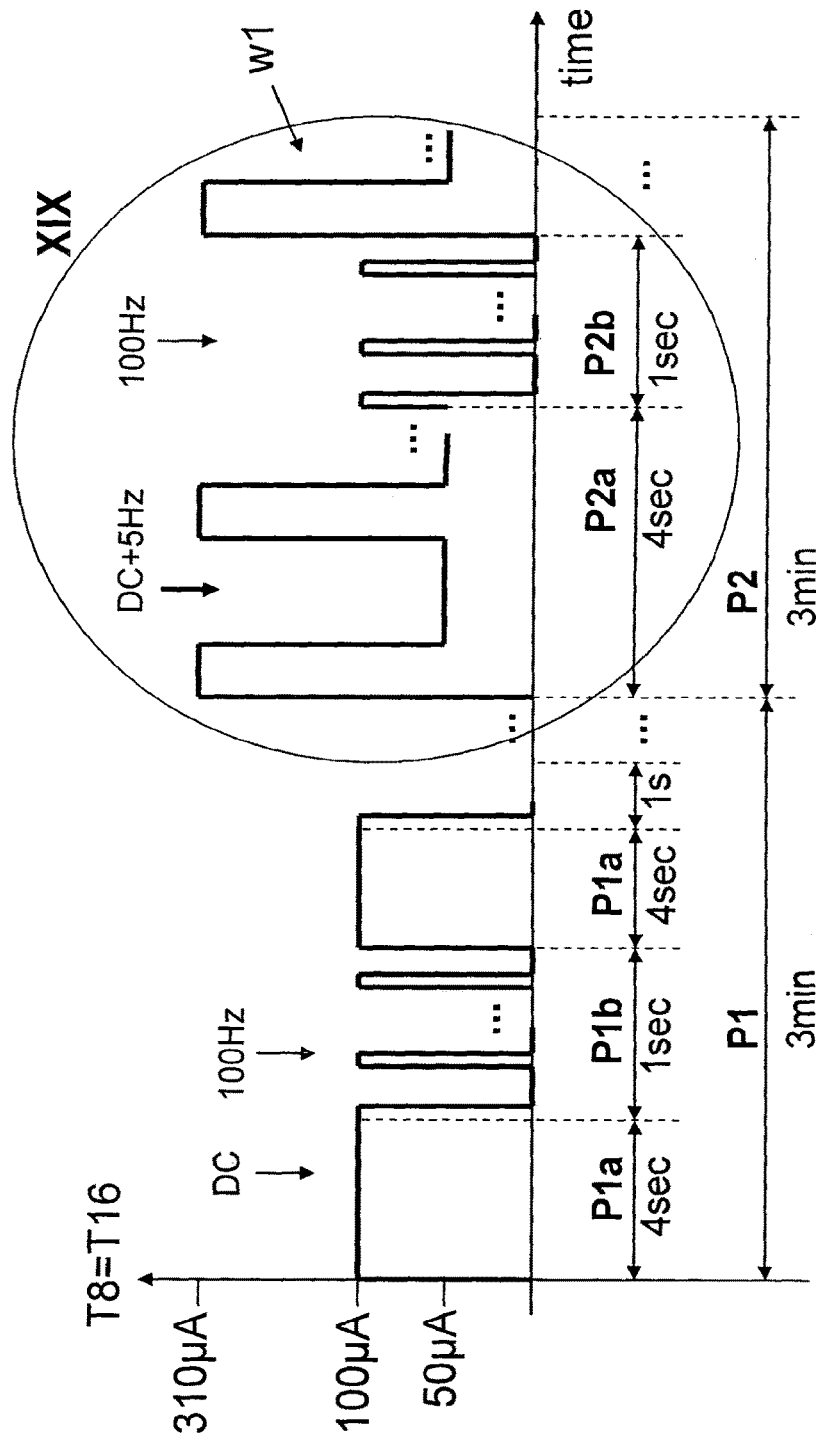
FIG. 18 shows a signal shape as a function of time, in accordance with signal type T8 and T16 of FIG. 9.

This is applied for example for signal type T8 of FIG. 9, the timing of which is reproduced in FIG. 10e. The corresponding signal shape w1 is reproduced in FIG. 18, and a part of it is also reproduced in greater detail in FIG. 19. For this signal therefore, both superimposition is applied for the first pulse train PT1 in the third period fractions P2a, and partitioning and substitution in the second and fourth period fractions P1b, P2b for the second pulse train PT2.

FIGS. 11A to 11D reproduce diagrammatically which signal parameters D1, f1, A1, B1, D2, f2, A2, B2 and time format [are] applied in the cases described above. The reduced parameter values D1*, A1*, A2* are not reproduced in these figures.

A Plurality of Electrodes Active in a Group at the Same Time

A method was described above for the generation of one signal shape w1 for electro-stimulation by means of one electrode E1, in which a plurality of therapeutic treatments can in fact be combined, as indicated by the indicators i1 to i4 in the encoding member 6.

The invention also provides a method of generating two or more signal shapes w1, w2 etc. for electro-stimulation by means of two or more electrodes E1, E2 etc. which can be connected to two or more wounds on the same body and which can be active at the same time. In this patent publication the term "group" is used for the set of electrodes which are active at the same time in the same active period Tact (for example 90 minutes).

In this case, in a first step f) a first signal shape w1 is generated for the first electrode E1 in a manner as described above in steps a) to e) inclusive and as illustrated in FIGS. 9 to 11A-11D, based upon the indicators of the first electrode E1. If we imagine for example that the indicators of the first electrode E1 contain the values i1=no, i2=yes, i3=yes, i4=yes, then signal type T8 will be formed for electrode E1, as indicated in FIG. 9.

After that, in step g) a check is repeatedly (i.e. for each port 5) made as to whether still more electrodes E2, E3 etc. are attached (for example by detecting whether the codeword cw can be retrieved by the other ports 5 of the apparatus 2), and a second signal shape w2 will be generated for the second electrode E2 in the same way as above. In this case the duration of the first period Tact1, the duration of the first and second period portions P1, P2 respectively and the duration of the first period fraction and the second, third and fourth period fractions P1a, P1b, P2a, P2b respectively of the further signal shape or shapes w2, w3 [are] selected to be equal to those of the first signal shape w1. In that way the combination of the signal shapes w1, w2 etc, can be limited to an analysis over the first period Tact1, the period portions P1, P2 and the period fractions P1a, P1b, P2a, P2b, and this makes the method much simpler both in terms of conception and in terms of implementation, as a result of which the processor speed can remain limited, and the service life of the battery is prolonged.

After that, in step h) a check is made for each first period Tact1, and period portion P1, P2 and period fraction P1a, P1b, P2a, P2b as to whether a plurality of pulse trains PT1, PT2 occur simultaneously in the signal shapes w1, w2, in which case the pulse trains may or may not be superimposed upon a DC signal, and, if they occur simultaneously, a shift d1, d2 is defined for each pulse train of each signal shape w1, w2, w3 in such a way that the pulses of the pulse trains no longer overlap in terms of time after shifting over the shifts d1, d2, and, after that, the shifts d1, d2 are associated with the first period, and the period portion and the period fractions with the simultaneous pulse train.

FIGS. 20A-20D indicate diagrammatically the possible procedure in this case. If for example the first signal shape w1 for the first electrode E1 should be of the signal type T3 (see FIG. 9), with a timing according to FIG. 20A, and if the second signal shape w2 for the second electrode E2 should be of the signal type T8 (according to FIG. 9), with a timing according to FIG. 20D, then the two first pulse trains PT1 (of for example 5 Hz) of the first and second signal shapes w1 and w2 will "occur simultaneously" in each third period fraction P2a, and the first pulse train PT1 (of for example 5 Hz) of the first signal shape w1 will occur simultaneously with the second pulse train PT2 (of for example 100 Hz) of the second signal shape w2 in each second and fourth period fraction P1b and P2b. If it is further imagined that the first pulse width B1 is equal to 2.0 ms and that the second pulse width B2 is equal to 1.0 ms, then by shifting the first pulse train PT1 from the second signal shape w2 into the third period fractions P2a over a first shift d1 in the range of from 2.0 to 198.0 ms, and by shifting the second pulse train PT2 from the second signal shape w2 into the second and fourth period fractions P1b and P2b over a second shift d2 in the range of from 2.0 to 9.0 ms, it is possible to prevent the pulses of the two signal shapes w1, w2 from overlapping in terms of time. It should be noted that in this example it is also possible to prevent pulse overlap by choosing both the first and the second shift d1, d2 to be equal to 2.0 ms for the second signal shape w2. It is preferable for the pulses of the first signal shape w1 not to be shifted.

Figure 20A:
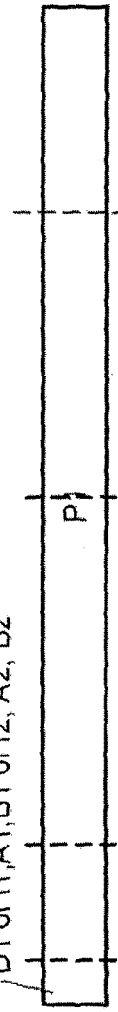
FIGS. 20A-20D are variants of FIGS. 11A-11D, respectively, and show in a diagrammatic manner which tests have to be carried out in the formation of a group of signal shapes.
Figure 20B:
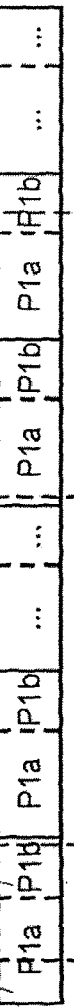
Figure 20C:
Figure 20D:

Let us consider as the second example that both the first and the second signal shape w1, w2 are of the signal type T8 (according to FIG. 9), both with a timing according to FIG. 20D. Then the first pulse trains PT1 (of 5 Hz) of the first and the second signal shape w1, w2 will "occur simultaneously" in the third period fractions P2a, and then the second pulse trains PT2 (of 100 Hz) will "occur simultaneously" in the second and fourth period fractions P1b, P2b of the two signal shapes w1, w2. The reader can easily determine this by placing the signal shape of FIG. 18 twice, one below the other. The overlap of the pulses of the second pulse train PT2 can be prevented by shifting the second pulse train PT2 in each second and fourth period fraction P1b, P2b by way of a second shift d2 in such a way that B2≤the second shift d2≤(1/f2)−B2, and so 1.0≤d2≤9.0 ms, for example 1.0 ms. A similar reasoning can be followed in order to prevent overlap of the pulses of the first pulse train PT1. If the first pulse frequency f1=5.0 Hz and the first pulse width B1=2.0 ms, then values d1 can be chosen in the range of from 2.0 to 198.0 ms for the first shift d1 of the first pulse trains PT1. By choosing d1=2.0 ms for example and by choosing d2=1.0 ms, overlap of the pulses can be prevented. It should be noted that in this example too it is possible to prevent pulse overlap by choosing both the first and the second shift d1, d2 to be equal to 2.0 ms for the second signal shape w2.

In an example with three electrodes E1, E2, E3, in which the indicators of each electrode indicate a signal type T8, overlap of the pulses can be prevented by choosing the values d1=2.0 ms and d2=1.0 ms for example for the second signal shape w2, and by choosing the values d1=4.0 ms and d2=2.0 ms for the third signal shape w3. It should be noted that pulse overlap should also be prevented by giving the value 2.0 ms to both the first and the second shift d1, d2 of the second signal shape w2 and giving the value 4.0 ms to the first and the second shift d1, d2 of the third signal shape w3.

In general it can be assumed that pulse overlap can be prevented in advance for any signal type T1 to T16 of FIG. 9, by choosing the first and the second shift d1, d2 of the second signal shape w2 to be equal to the greater of the first and the second pulse width B1, B2 (in the example above 2.0 ms), and two times this value for the third signal shape w3 (in the example above 4.0 ms), and three times this value for the fourth signal shape w4 and so forth, in which case, however, the shift may not be greater than (1/f2)−B2, being 9.0 ms in the example above.

After that, a check is made in step i) for each first period Tact1 and period portion P1, P2 and period fraction P1a, P1b, P2a, P2b as to whether a plurality of DC signals occur simultaneously in the signal shapes w1, w2 etc., and if that is the case then a first sum Σ1 is calculated from the DC values D of the simultaneously occurring DC signals, and if this first sum Σ1 is greater than a first maximum value M1 (for example 500 μA), then a first scale factor α is calculated as a proportion of the first sum Σ1 and the first maximum value M1, and this first scale factor α is then associated with the respective first period or period portion or period fraction with the simultaneous DC signal. The first maximum value M1 is preferably a value of from 500 to 750 μA, in a more preferred manner approximately equal to 500 μA.

As an example, if it is supposed that M1=500 μA and that the first and the second signal shapes w1, w2 are both of the signal type T9 (according to FIG. 9, and so both are a DC signal of 400 μA), then the first sum Σ1 of the DC values D is equal to 800 μA, which is greater than 500 μA. If the scale factor α is calculated as the sum divided by the maximum value Σ1/M1, then it is possible for the scale factor to be applied later (in step m, see below) by dividing the DC signals by the scale factor, as a result of which the two DC values should be reduced to a value of 250 μA in this example. If, as an alternative, the scale factor α is calculated as the maximum value divided by the sum M1/Σ1, then it is possible for the scale factor α to be applied later (in step m) by multiplication with the scale factor, and this should lead to the same result.

In an example with one signal shape w1 of the type T5 and four signal forms w2 to w5 of the type T8, simultaneous DC signals occur in the entire first period Tact1 of w1, and in each first and third period fraction P1a, P2a of w2 to w5, and the first scale factor α should be associated with the entire first period of w1, but in w2 to w5 associated only with the first period fraction P1a since there the first sum Σ1 is equal to 600 µA, whereas over the third period fractions the first sum Σ1 is equal to only 300 µA. In this example the first scale factor α is therefore not associated with the third period fractions P2a of w2 to w5. The result (in step m) will be that the DC value of w1 (over the entire first period Tact1) is scaled to 83.3 µA, and that the DC value in the first period fraction P1a of w2 to w5 is also scaled to 83.3 µA, but the DC value (of 50 µA) in the third period fraction P2a of w2 to w5 is not scaled.

After that, a check is made in step j) for each first period Tact1 and period portion P1, P2 and period fraction P1a, P1b, P2a, P2b as to whether at least one DC signal and at least one pulse train PT1, PT2 occur simultaneously in the signal shapes w1, w2, w3, and if that is the case, then a DC component AG1, AG2 is calculated from each simultaneous pulse train by multiplying the pulse amplitude A1, A2 with the averaged duty cycle of the pulse train in question, and a second sum Σ2 is calculated from the DC values D and the DC components AG1, AG2 of the simultaneously occurring DC values and pulse trains, and if the second sum Σ2 is greater than a second maximum value M2 (for example 600 µA), then in the first instance all the DC values D which are greater than a limiting value K (for example 100 µA) are limited to the limiting value K, and then the limiting value K is associated with the period and period portion and period fraction with the simultaneous DC signal with a DC value greater than the limiting value K. After that, the second sum is recalculated, whilst taking into consideration the limited DC values, and if the recalculated second sum (Σ2') is greater than the second maximum value M2, then a second scale factor β is calculated as a proportion of the recalculated second sum Σ2' and the second maximum value M2, and then associated with the period and period portion and period fraction with the simultaneously occurring DC value and pulse train. It is preferable for the second maximum value M2 to be a value of from 500 to 750 µA, preferably approximately 600 µA. The limiting value K is preferably a value of from 100 to 200 µA, and in a more preferred manner approximately 100 µA.

Let us take by way of example an apparatus with two electrodes E1, E2, in which the first signal shape w1 for the first electrode E1 is a DC signal with a DC value of 400 µA (signal type T9 of FIG. 9, with the timing of FIG. 20A) and the second signal shape w2 for the second electrode E2 is a second pulse train PT2 of 100 Hz with a second pulse amplitude A2 of 400 µA and a second pulse width B2 of 1 ms (signal type T2 of FIG. 9 with the timing of FIG. 20A), and that the second maximum value M2 is selected as 600 µA. In this case a DC signal and a pulse train occur simultaneously in the entire first period Tact1. The second sum Σ2 is then 400 µA+(400 µA*1/10)=440 µA. This is smaller than the second maximum value M2 of 600 µA, and as a result no second scale factor β is calculated or associated. The signal shapes w1, w2 can at the same time occur unchanged.

As a second example, let us suppose that the apparatus 2 should have four electrodes E1, E2, E3, E4, and that the signal shapes w1, w2 for the electrodes E1 and E2 should be of the signal type T9, and that the signal shapes w3, w4 for the electrodes E3 and E4 should be of the signal type T2. (It should be noted that in this example the signal shapes are the same as in the previous example, but the number of electrodes is doubled.) In this case a DC signal and a pulse train occur simultaneously in the entire first period Tact1. The second sum Σ2 is 2*(400 µA (400 µA*1/10))=880 µA. This is higher than the second maximum value M2 of 600 µA, and so the DC values of 400 µA are first reduced to the limiting value K of 100 µA, and the limiting value K is associated with the first period Tact of the signal shapes w1 and w2. After that, the second sum is calculated once again as: 2*(100 µA+(400 µA*1/10))=280 µA. This is lower than the second maximum value M2 of 600 µA, and so no second scale factor β is calculated or associated with the signal shapes. The result in step m will be that the signal shapes w1 and w2 of the type T9 are limited to a DC value equal to the limiting value K (100 µA). The pulse amplitude of the signal shapes w3 and w4 remain unchanged, but they are in fact shifted (see above). The four adjusted signal shapes w1° to w4' can occur simultaneously without exceeding the therapeutic limiting values.

Let us suppose as a third example, that the apparatus has twelve electrodes E1 to E12, and that the signal shapes w1 to w6 for the electrodes E1 to E6 are of the signal type T9 (of FIG. 9), and that the signal shapes w7 to w12 for the electrodes E7 to E12 are of the signal type T3 (of FIG. 9). In this case a DC signal and a pulse train occur simultaneously in the entire first period Tact1. The second sum Σ2 is now 6*(400 µA+(400 µA *2/200)=2424 µA. This is higher than the second maximum value M2 of 600 µA, and so the DC values of 400 µA are first reduced to the limiting value K of 100 µA, and the second sum is calculated once again as: Σ2'=6*(100 µA+(400 µA*1/100)) 624 µA. This is still higher than the second maximum value M2 of 600 µA. The second scale factor β is calculated as the recalculated sum divided by the second maximum value β=Σ2'/M2=624/600=1.04, and is associated with all the signal shapes w1 to w12. The limiting value K is associated with the signal shapes w1 to w6. The result in step m, after applying the scale factor β and the limiting value K, is that the eventual signal shapes w1 to w6 have a DC value of 100/1.06=94.3 µA, and the signal shapes w7 to w12 have a second pulse amplitude of 400/1.06=377 µA. In step m the second pulse trains of w2 to w6 are also shifted as described above, for example over 2, 4, 6, 8 and 10 ms respectively). The adjusted signal shapes w1' to w12' can occur simultaneously.

It is preferable for the second maximum value M2 to be selected to be slightly greater (for example from 50 to 100 µA) than the first maximum value M1, since the influence of the pulse amplitudes because of the duty cycle is much less in the sum than the DC values.

The method according to the invention could be further optimized by choosing a plurality of limiting values K1, K2, K3, for example 300, 200 and 100 µA, and by recalculating the second sum Σ2 once again before applying the second scale factor β. As a result, the decrease from 400 µA to 100 µA should be less drastic, and can be applied in stages.

After that, a check is made in step k) into whether more electrodes E3, E4 are still attached to the apparatus 2, and the steps f) to j) inclusive from above are also repeated for these electrodes.

Finally, in step i) the signal shapes w1, w2, w3 of the group G1 are adjusted in each period and period portion and period fraction,
  by shifting the pulse trains PT1, PT2 over the associated shifts d1, d2 if a shift d1, d2 is associated with the first period or period portion or period fraction, and by limiting the DC values D greater than the limiting value K to the limiting value K if the limiting value K is associated with the first period or period portion or period fraction, and by scaling the DC values D, K with the first scale factor α if the first scale factor α is associated with the first period or period portion or period fraction, and by scaling the limited DC values D, K and the pulse amplitudes A1, A2 with the second scale factor β if the second scale factor β is associated with the first period or period portion or period fraction.

By not letting the pulses on the various channels overlap in terms of time, a step is taken to minimize mutual influence of currents of different electrodes, so that the current densities locally in the tissue do not exceed the maximum therapeutic values.

By reducing and/or scaling the signal values, the method ensures that the total sum of the currents through the electrodes E1, E2 etc. used remains within defined limits. In this way, it has been demonstrated for example in studies that when the current density goes above 2000 μA the production of adenosine triphosphate is lower than without applying electric current. Since the body is not a homogeneous conductor and the actual flow paths are not predictable, problems of this type are prevented by the method according to the invention.

A Plurality of Groups

The method according to the invention can optionally be further extended. In this case, in step h) from above a further test is made into whether the associated first or second shift d1, d2 respectively is greater than a previously defined first or second maximum shift dmax1, dmax2 respectively (dmax1 is for example 197 ms in the example from above), (dmax2 is for example 9 ms in the example from above);

and in step i) a further test is made into whether the DC value D of at least one signal shape w1, w2 after scaling with the first scale factor α is smaller than a first minimum value m1 (for example 50 μA);

and in step j) a further test is made into whether the pulse amplitude A of at least one signal shape w1, w2 after scaling with the second scale factor β is smaller than a second minimum value m2 (for example 50 μA);

and if one of these tests is met, then at least one signal shape from the first group G1 is removed, and the signals of the first group G1 are recalculated, and a second group G2 is formed for the remaining signal shapes, and the signal shapes of the first and the second group G1, G2 are shifted with respect to one another (for example over a duration of 90 minutes) in such a way that the signal shapes of the first group G1 are active in a first active period Tact1 (for example the first 90 minutes) in which the signal shapes of the second group G2 are at rest, and in which the signal shapes of the second group G2 are active in a second active period Tact2 (for example the second 90 minutes) which does not overlap with the first active period Tact1 and in which the signal shapes of the first group G1 are at rest.

Figure 22:
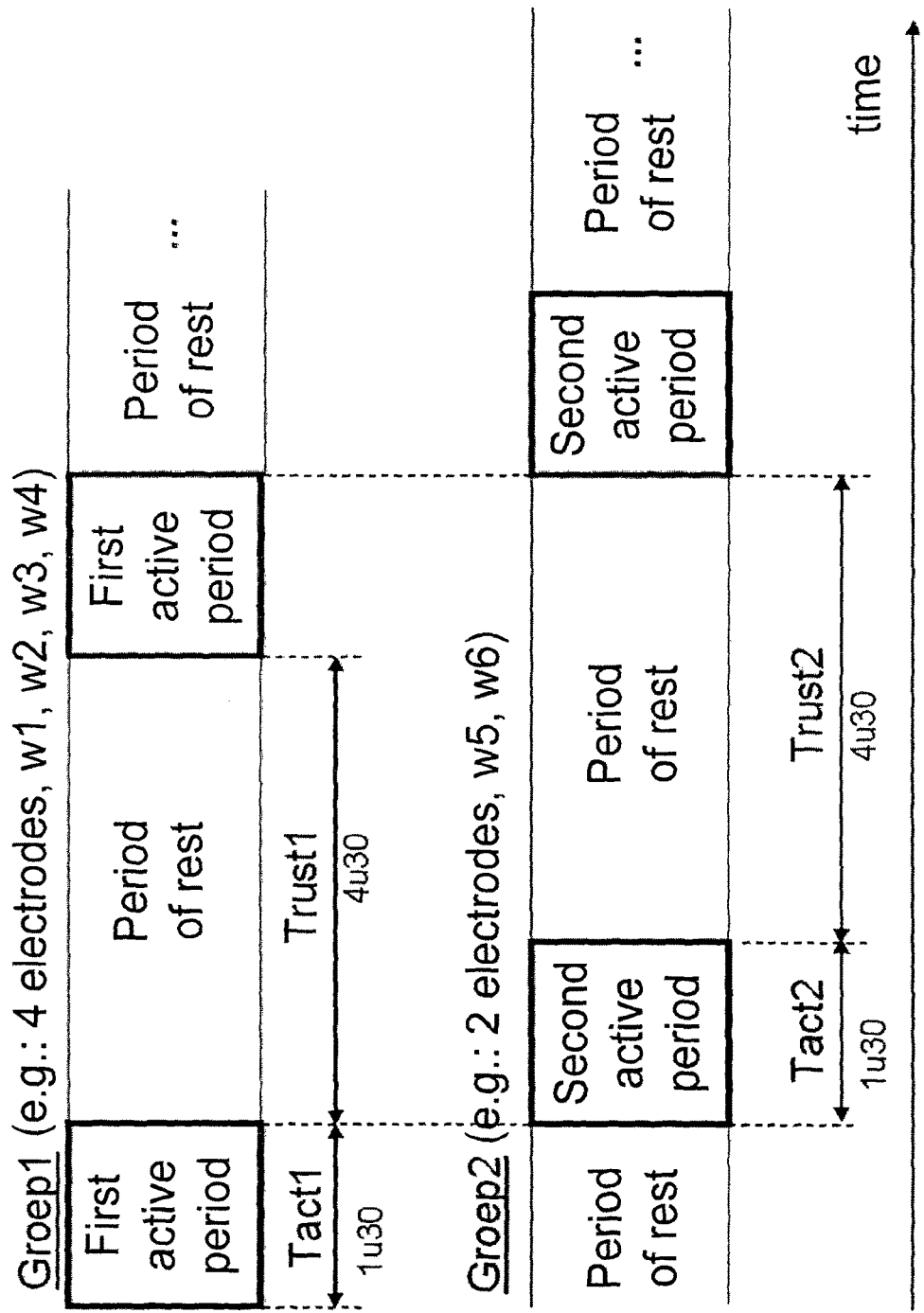
FIG. 22 shows an example of two groups of signals formed by the method according to the invention, in which four electrodes of the first group are active in a first active period, and two electrodes of the second group are active in a second active period.

FIG. 22 shows an example in which a first group G1 of four signal shapes w1 to w4 for four electrodes E1, E2, E3, E4 is active during a first active period Tact1 (for example 90 minutes), after which a second group G2 of two signal shapes w5, w6 for electrodes E5, E6 is active during a second active period Tact2 (for example likewise 90 minutes); after which a period of rest of example 3 hours follows, after which the cycle is repeated.

It is preferable for the first minimum value m1 to be a value of from 25 to 50 μA, in a more preferred manner approximately 50 μA. If the DC value becomes too small, it no longer has an adequate therapeutic effect.

It is preferable for the second minimum value m2 to be a value of from 25 to 50 μA, in a more preferred manner approximately 50 μA. If the pulse amplitude becomes too small, it no longer has an adequate therapeutic effect, as shown in FIGS. 7 and 8.

The method according to the invention could be further optimized by a more uniform distribution of the signal shapes over the plurality of groups, once it has become apparent that the signals cannot be formed in one group. In an alternative embodiment a check could first be made into how many groups G1, G2 need to be formed, after which the signal shapes can be distributed over the groups, and finally the signal shapes of each group can be calculated as described above.

Assembly

The invention also relates to an assembly 1 for healing wounds by electro-stimulation, comprising at least one electrode E1 which is connected to an encoding member 6 in which a code word cw has been saved, the code word cw comprising at least two code word portions c1, c2, and the first and the second code word portion identifying a first and a second therapeutic treatment tb1, tb2 respectively, and the first and the second code word portion having coupled to them a first and a second indicator i1, i2 respectively which indicates whether the therapeutic treatment (tb1, tb2) associated with the code word portion in question should be activated or not;

an electronic apparatus 2 with at least one port 5 for connecting the apparatus 2 to the electrode E1, and with a data-processing unit 3 connected to the port for retrieving the code word cw from the encoding member 6, and for defining the associated therapeutic treatments tb1, tb2 on the basis of the code word portions c1, c2 and for checking the activation of the indicators i2, and with a signal shape generator 23 with a memory for retrieving a first and a second signal s1 associated with the first and the second therapeutic treatment tb1, tb2 respectively, and with a buffer for the formation and the further formation of a temporary signal shape w, and with a clock circuit for the generation of the signal shape w1.

Figure 23:
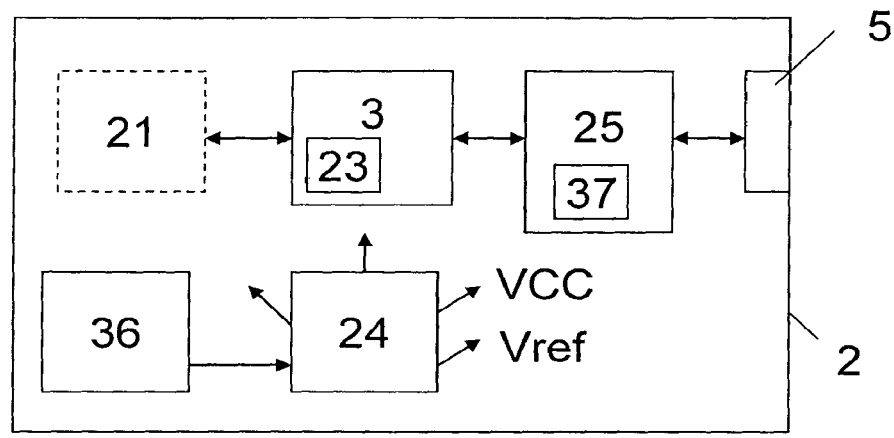
FIG. 23 reproduces a block diagram of an electronic apparatus according to the invention.

FIG. 23 is a block diagram of an embodiment of the electronic apparatus 2 according to the invention.

It contains a battery 36 for delivering energy to the apparatus 2, and a feed module 24 for producing internal voltages such as VCC and a reference voltage Vref of for example 1.0 V. VCC is for example a DC voltage in the order of magnitude of 15 V, which is derived from the battery voltage by means of known DC to DC converters such as a "boost converter" or a "charge pump". This voltage is necessary for the micro-current module 37 (which will be further described in FIG. 24).

The apparatus 2 optionally further contains a user interface 21 with optionally one or more switches, optionally an LCD display for example in order to indicate the status of the battery, and/or optionally one or more LEDs, for example in order to indicate an alarm situation, and if necessary a buzzer or other source of noise, or a time indicator so that the progress of the therapy can be followed by the patient or a nurse. In one embodiment a switch can be provided in order to switch the apparatus ON or OFF. In this way it is possible for the battery voltage to be saved. In one embodiment the feedback to the user is restricted to single LEDs which indicate that the device has been switched on, the battery still has sufficient capacity, an electrode is connected, or is not actively occupied with therapy, and whether an error condition has occurred (for example the electrode E1 detached from the body, a connector incorrectly pulled out, a defect in the apparatus 2, etc.). In an extended version this information can be indicated on a display (for example an LCD), in which the necessary information such as the duration of the treatment and the status of the battery can be displayed numerically. It is also preferable for an acoustic signal to be provided in order to signal successful actions (for example the attachment of connectors) as well as to signal error conditions as indicated above.

The apparatus 2 further contains a data-processing unit, for example a micro-processor 3 with a memory and with software code fragments for the control and checking of the other modules 21, 25. The data-processing unit can contain the following functions for example: dealing with the user input (switches and/or connectors), control of LEDs and/or display, control of the micro-current module 37 for the various micro-currents for the various electrodes E1, E2 etc., in order to control the timing (for example of the micro-current module 37 or switching off channels), monitoring of the battery voltage, indication of error conditions, and optionally the saving (logging) of data, and optionally external communication.

The apparatus 2 further contains a signal shape generator 23 for the generation of signal shapes w1, w2 in accordance with the method as described above, on the basis of parameters such as the DC value D, the pulse frequency f, the pulse amplitude A, the pulse width B, the pulse shift d, provided by the data-processing unit 3. The signal shape generator 23 can be implemented in software for example, or can be a hardware component on the inside or outside with respect to the data-processing unit 3. The signal shape generator 23 is connected to a connection module 25 which contains the micro-current module 37 for the production of a micro-current derived from the generated signal shape w1. The micro-current will be connected to a pin 8 of a port to which an electrode E is connected (for example the uppermost pin 8e in the connector 4 of FIGS. 25 and 26). In addition, the connection module 25 is provided with means for reading the code word cw from an encoding member 6 by way of a port 5 of the apparatus 2, and in order to pass the code word cw and the associated indicators i1 to i4 on to the data-processing unit 3. The connection module 25 is also optionally provided with means to check whether an electrode E has been connected to a port 5 of the apparatus 2, and whether this electrode is making sufficient contact so that a micro-current can flow. In addition, the apparatus 2 comprises a clock circuit (not shown) for the generation of the timing. This can be for example an RC circuit, or a circuit with a crystal module, or a "real time" clock circuit, but it is preferably an internal clock in the micro-processor 3.

The signal shape generator 23 is capable of being set by way of the data-processing unit 3 and will deliver one or more signal shapes w1, w2 in accordance with the method as described above.

Figure 24:
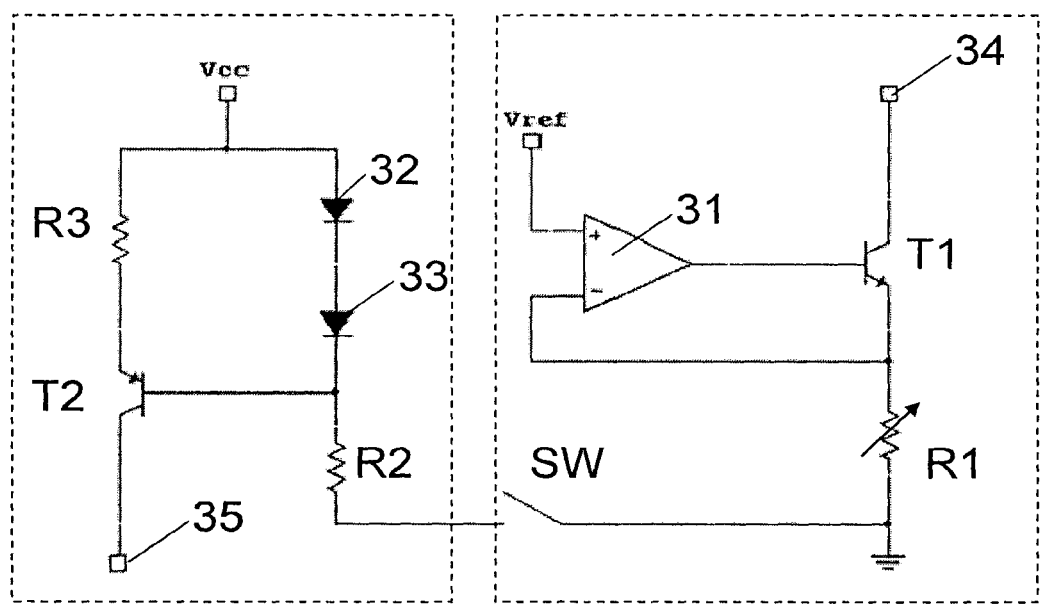
FIG. 24 shows a possible embodiment of the microcurrent circuit as a part of the electronic apparatus as shown in FIG. 23.

FIG. 24 is a block diagram of a micro-current module 37 as can be used in the apparatus 2 according to the present invention. This circuit is used to deliver a micro-current when an external load is applied by way of the connection points 34, 35. The micro-current has a shape corresponding to the signal shape w1 which is generated by the signal shape generator 23. If the electrode E1 is connected to the port 5 of the apparatus 2, and if, however, the load applied (impedance) rises above a maximum value (for example 10K ohms or 300K ohms or more), the micro-processor 3 will preferably actuate an alarm in order to indicate that the electrode E1 has not been correctly connected to the body.

The circuit operates as follows: the right-hand side of the drawing shows a so-called "current sink". The connection point 34 is connected to the collector of an NPN transistor T1, which is controlled by the output of an operational amplifier 31. The latter will attempt to control its output in such a way that the voltage over the first resistor R1 is equal to the reference voltage Vref of for example 1.0 volt. As a result of altering the resistance value of R1 the amperage can be set by the transistor T1. This can be implemented for example by the resistor R1 as a network of resistor ladders which for example is capable of being set from the signal shape generator 23 or from the micro-processor 3 on the basis of the generated signal shape w1. The left-hand side of FIG. 25 shows a current limiter. The voltage VCC, for example 15 volts, is applied on one side by way of two diodes 32, 33 in series with a second resistor R2, in order to create a voltage division of on the one hand virtually 1.4 volts over the diodes, and approximately 13.6 volts over the second resistor R2. This latter has no further relevance for the operation of the circuit. The voltage VCC is also applied to the emitter of a second transistor T2, a PNP transistor, by means of a third resistor R3. The base of this transistor T2 is connected to the voltage divider. With a normal load between the contacts 34 and 35 (for example 10 K ohm) a current flows through the transistor T2 and through the third resistor R3 in such a way that the emitter base voltage over the transistor T2 amounts to approximately 0.7 volts. When the external load becomes greater (greater impedance), the current through the second transistor T2 and through the third resistor R3 will drop, as a result of which the base emitter voltage increases, and this will bring the second transistor T2 too into conductance. Conversely, when the external load becomes smaller (lower impedance), the current through the second transistor T2 and through the third resistor R3 will become greater, but since the base voltage is (virtually) constant the second transistor T2 will be blocked. This circuit thus acts as a current limiter. The electrode E1 is attached for example to the connection point 34, and the central contact (as illustrated in FIGS. 1 to 4) is attached for example to the connection point 35. The "current sink" is set up around the PNP transistor T2 which can be switched on by connecting the second resistor T2 to earth, for example by means of the switch S controlled by the microprocessor. In this way, the microprocessor can switch off certain channels in order to save energy. A first embodiment of the apparatus 2 according to the invention meets the standards EN 60601-1-x, in which x=1-5.

It is preferable for the electrode E1 to comprise a connector 4 which comprises the encoding member 6, and for the electronic apparatus 2 to comprise at least one port 5 for receiving the connector 4. In this way, a suitable electrode E1 with the desired indicators i1 to i4 can be selected and connected to the apparatus 2.

In one embodiment the encoding member 6 [comprises] at least one wire jumper 7 between various pins 8 of the connector 4, and the value of the indicator i1, 12 is defined by the presence of the at least one wire jumper between two pins 8. An example is shown in FIG. 25 which has already been discussed in combination with FIG. 2.

In one embodiment the encoding member 6 comprises a memory element chosen from the group of EPROM;

EEPROM, flash and RF-ID. An example is shown in FIG. 26 which has already been discussed in combination with FIG. 2.

Although the present invention has been described with reference to specific preferred embodiments, it will be obvious that various changes can be made to these embodiments without departing from the protective scope of the invention, as set out in the Claims. The description and drawings should consequently be regarded in an illustrative sense rather than in a restrictive sense.

The invention claimed is:

1. A method for generating signal shapes of electro-stimulation signals to be supplied to electrodes for healing wounds by micro-current electro-stimulation, the method comprising the steps of:
   a) connecting a first electrode to a first port of a signal shape generator, wherein the first electrode is connected to a first encoding member in which a first code word is stored, the first code word identifying at least one first therapeutic treatment to be applied by the first electrode,
   b) connecting a second electrode to a second port of the signal shape generator, wherein the second electrode is connected to a second encoding member in which a second code word is stored, the second code word identifying at least one second therapeutic treatment to be applied by the second electrode,
   c) connecting a central contact to a third port of the signal shape generator, the central contact being provided for contact with skin and for use as a return channel of microcurrents which are applied by the electrodes,
   d) positioning the first and second electrodes and the central contact for treatment of at least one wound,
   e) retrieving from the first and second encoding members the first and second code words,
   f) retrieving at least one first signal associated with the at least one first therapeutic treatment identified by the first code word and the formation of a first temporary signal shape on the basis of the at least one first signal,
   g) retrieving at least one second signal associated with the second therapeutic treatment identified by the second code word and the formation of a second temporary signal shape on the basis of the at least one second signal,
   h) checking the first and second temporary signal shapes in order to establish whether or not the combination of the first and second temporary signal shapes falls within therapeutic limits of the therapeutic treatments identified by the code words,
   i) adjusting at least one of the first and second temporary signal shapes so as to fall within the therapeutic limits if it has been established that the combination of the first and second temporary signal shapes did not fall within the therapeutic limits, and
   j) forming, by the signal shape generator, first and second wound healing electro-stimulation signals on the basis of respectively the first temporary signal shape and the second temporary signal shape and applying the first and second wound healing electro-stimulation signals to respectively the first electrode and the second electrode, the first and second wound healing electro-stimulation signals being micro-current signals having an amplitude of less than 1 mA,
   wherein at least one of the first and second code words comprises at least four code word portions, wherein the first code word portion identifies an antibacterial treatment, the second code word portion identifies a cell migration treatment, the third code word portion identifies a treatment for pain and/or a treatment for the increase in the oxygen tension TcPO2, and the fourth code word portion identifies a stimulation of one or more processes selected from the group consisting of ATP production, DNA production, protein production, and amino acid absorption.

2. The method according to claim 1,
   wherein the first temporary signal shape comprises a first DC signal with a first direct current (DC) value during a first period, and wherein the second temporary signal shape comprises a second DC signal with a second DC value during a second period not overlapping with the first period, and
   wherein the adjustment comprises changing the first DC value to a third DC value lying in a range with the first DC value and the second DC value as the limit values.

3. The method according to claim 2, wherein the adjustment of the first DC value is setting the first DC value equal to the smallest DC value of the first DC value and the second DC value.

4. The method according to claim 1,
   wherein the first temporary signal shape comprises a first direct current (DC) signal with a first DC value during a first period,
   wherein the second temporary signal shape comprises a first pulse train with a first frequency lower than a predetermined frequency and with a first pulse amplitude and with a first pulse width, the first pulse train being active during a second period not overlapping with the first period, and
   wherein the adjustment comprises either reducing the first DC value to a reduced DC value or reducing the first pulse amplitude to a reduced first pulse amplitude.

5. The method according to claim 4, wherein the predetermined frequency is a frequency in the range of from 20 to 50 Hz.

6. The method according to claim 4, wherein the predetermined frequency is a frequency substantially equal to 30 Hz.

7. The method according to claim 1,
   wherein the first temporary signal shape comprises a first pulse train with a first frequency lower than a predetermined frequency and with a first pulse amplitude and with a first pulse width, and
   wherein the second temporary signal shape comprises a second pulse train with a second frequency higher than the predetermined frequency and with a second pulse amplitude and with a second pulse width, the second pulse train being active during a second period not overlapping with the first period.

8. The method according to claim 1,
   wherein at least one of the first and second code words comprises a plurality of code word portions, and
   wherein each code word portion respectively identifies a different therapeutic treatment.

9. The method according to claim 1,
   wherein one of the therapeutic treatments is an antibacterial treatment, and
   wherein a direct current (DC) signal with a DC value of from 4 to 750 µA is selected as the signal associated with this therapeutic treatment.

10. The method according to claim 1,
    wherein one of the therapeutic treatments is an antibacterial treatment, and wherein a direct current (DC) signal with a DC value of from 300 to 500 μA is selected as the signal associated with this therapeutic treatment.

11. The method according to claim 1,
wherein one of the therapeutic treatments is an antibacterial treatment, and
wherein a direct current signal with a DC value of approximately 400 μA is selected as the signal associated with this therapeutic treatment.

12. The method according to claim 1,
wherein one of the therapeutic treatments is a cell migration treatment, and
wherein a direct current (DC) signal with a DC value of from 50 to 750 μA is selected as the signal associated with this therapeutic treatment.

13. The method according to claim 1,
wherein one of the therapeutic treatments is a cell migration treatment, and
wherein a direct current signal with a DC value of approximately 100 μA is selected as the signal associated with this therapeutic treatment.

14. The method according to claim 1,
wherein one of the therapeutic treatments is a treatment for pain and/or a treatment for the increase in the oxygen tension TcPO2, and
wherein a first pulse train with a first frequency of from 0.2 to 20.0 Hz, with a first pulse amplitude of from 10 to 750 μA, and with a first pulse width of from 0.1 to 2.0 ms, is selected as the signal associated with this therapeutic treatment.

15. The method according to claim 1,
wherein one of the therapeutic treatments is a treatment for pain and/or a treatment for the increase in the oxygen tension TcPO2, and
wherein a first pulse train with a first frequency of approximately 5.0 Hz, with a first pulse amplitude of from 100 to 400 μA, and with a first pulse width of from 1.0 to 3.0 ms, is selected as the signal associated with this therapeutic treatment.

16. The method according to claim 1,
wherein one of the therapeutic treatments is a stimulation of a process selected from the group of ATP production, DNA production, protein production, and amino acid absorption, and
wherein a second pulse train with a second frequency of from 50 to 160 Hz, with a second pulse amplitude of from 10 to 750 μA, and with a second pulse width of from 0.1 to 5.0 ms, is selected as the signal associated with this therapeutic treatment.

17. The method according to claim 1,
wherein one of the therapeutic treatments is a stimulation of a process selected from the group of ATP production, DNA production, protein production, and amino acid absorption, and
wherein a second pulse train with a second frequency of approximately 100 Hz, with a second pulse amplitude of from 100 to 400 μA, and with a second pulse width of from 0.2 to 2.0 ms, is selected as the signal associated with this therapeutic treatment.

18. The method according to claim 1,
wherein the first temporary signal shape comprises a first pulse train with a first frequency, with a first pulse amplitude, and with a first pulse width, the first pulse train being active during a first period,
wherein the second temporary signal shape comprises a second pulse train with a second frequency and second pulse amplitude and with a second pulse width, the second pulse train being active during a second period not overlapping with the first period, and
wherein the adjustment comprises shifting the second temporary signal shape in time, such that pulses of the first and second pulse trains do not overlap after the shifting.

* * * * *